(12) United States Patent
Takano et al.

(10) Patent No.: US 8,583,452 B2
(45) Date of Patent: *Nov. 12, 2013

(54) HEALTH CHECK SYSTEM, HEALTH CHECK APPARATUS AND METHOD THEREOF

(75) Inventors: Kosuke Takano, Kanagawa (JP); Naofumi Yoshida, Kanagawa (JP); Shuichi Kurabayashi, Kanagawa (JP)

(73) Assignee: Empire Technology Development LLC, Wilmington, DE (US)

( * ) Notice: Subject to any disclaimer, the term of this patent is extended or adjusted under 35 U.S.C. 154(b) by 880 days.

This patent is subject to a terminal disclaimer.

(21) Appl. No.: 12/640,967

(22) Filed: Dec. 17, 2009

(65) Prior Publication Data
US 2010/0234694 A1 Sep. 16, 2010

(30) Foreign Application Priority Data

Mar. 13, 2009 (JP) ................................ 2009-060545

(51) Int. Cl.
*G06Q 10/00* (2012.01)
*G06F 3/00* (2006.01)

(52) U.S. Cl.
USPC .............................................. 705/2; 719/321

(58) Field of Classification Search
USPC .............. 600/300, 301; 705/2, 3, 4, 51, 26, 1, 705/26.5; 709/201, 207, 245, 217; 719/321, 719/322, 327
See application file for complete search history.

(56) References Cited

U.S. PATENT DOCUMENTS

| | | | |
|---|---|---|---|
| 6,886,045 B1 | 4/2005 | Halasz et al. | |
| 8,184,170 B2 | 5/2012 | Yamaji | |
| 2002/0084675 A1 | 7/2002 | Buchanan et al. | |
| 2003/0013438 A1* | 1/2003 | Darby ........................... 455/419 |
| 2003/0069752 A1* | 4/2003 | LeDain et al. .................... 705/2 |

(Continued)

FOREIGN PATENT DOCUMENTS

| | | |
|---|---|---|
| JP | 09-296772 | 11/1997 |
| JP | 2001-216315 | 8/2001 |

(Continued)

OTHER PUBLICATIONS

Kurabayashi, Shuichi et al., "Active Multidatabase System for Mobile Computing Environment," *Information Processing Society of Japan*, The Special Interest Group Technical Reports of IPSJ 2000-DBS-122, 2000, 9 pages (with English abstract), Abstract Only.

(Continued)

*Primary Examiner* — Lena Najarian
*Assistant Examiner* — Natalie A Pass
(74) *Attorney, Agent, or Firm* — Foley & Lardner LLP

(57) ABSTRACT

Various types of health checks are realized using optimal sensors. The health check apparatus according to the present application is configured such that optimal sensors 160 corresponding to an environment or the like in which an information service is realized out of a plurality of available sensors 160 or sensors 160 available to realize a health check to be delivered are selected. The health check apparatus according to the present application selects appropriate parameters for the sensors 160 and processing programs 286, 300 and 310 so that a health check is appropriately delivered and sets the parameters in the sensors and processing programs. Thus, the health check apparatus according to the present application is configured to be able to deliver various health checks by only receiving specification of a desired information service by the user and thereby appropriately combining various types of sensors and a plurality of processing programs.

19 Claims, 21 Drawing Sheets

| SERVICES | SENSORS FOR SERVICE AND THEIR PRIORITIES | | | | | | | | | | | | | | | SETS OF MODULES FOR SERVICES | PROPERTIES OF SERVICES |
|---|---|---|---|---|---|---|---|---|---|---|---|---|---|---|---|---|---|
| | 162 | 164 | 166 | 168 | 170 | 172 | 174 | 176 | 178 | 180 | 182 | 184 | 186 | 190-1 | 190-n | | |
| S#1 (HEALTH CHECK) | 0 | 3 | 1 | 0 | 0 | 2 | 0 | 0 | 0 | 0 | 0 | 0 | 0 | 0 | 0 | MS#1 | 2 |
| S#i (NAVIGATION) | 0 | 0 | 0 | 0 | 0 | 0 | 0 | 1 | 2 | 2 | 2 | 0 | 0 | 0 | 0 | MS#i | 1 |
| S#i+1 (IMAGE INFORMATION) | 0 | 0 | 0 | 0 | 0 | 0 | 0 | 1 | 2 | 2 | 2 | 0 | 0 | 0 | 0 | MS#i+1 | 4 |
| S#j | $N_{j1}$ | $N_{j2}$ | $N_{j3}$ | $N_{j4}$ | $N_{j5}$ | $N_{j6}$ | $N_{j7}$ | $N_{j8}$ | $N_{j9}$ | $N_{j10}$ | $N_{j11}$ | $N_{j12}$ | $N_{j13}$ | $N_{j14}$ | $N_{jk}$ | MS#j | 1 |
| S#n | $N_{n1}$ | $N_{n2}$ | $N_{n3}$ | $N_{n4}$ | $N_{n5}$ | $N_{n6}$ | $N_{n7}$ | $N_{n8}$ | $N_{n9}$ | $N_{n10}$ | $N_{n11}$ | $N_{n12}$ | $N_{n13}$ | $N_{n14}$ | $N_{nk}$ | MS#n | 3 |

(56) References Cited

U.S. PATENT DOCUMENTS

| | | | |
|---|---|---|---|
| 2004/0040771 | A1 | 3/2004 | Ploucha |
| 2005/0011129 | A1 | 1/2005 | Vassy |
| 2006/0056625 | A1 | 3/2006 | Nakabayashi et al. |
| 2006/0109734 | A1* | 5/2006 | Fukuda et al. ............ 365/232 |
| 2006/0287889 | A1* | 12/2006 | Brown ........................ 705/2 |
| 2007/0218862 | A1* | 9/2007 | Tatman et al. ............. 455/403 |
| 2008/0194925 | A1* | 8/2008 | Alsafadi et al. ............ 600/301 |
| 2008/0225137 | A1 | 9/2008 | Kubo et al. |
| 2008/0239083 | A1 | 10/2008 | Kusaka et al. |
| 2008/0256214 | A1* | 10/2008 | Halasz et al. .............. 709/207 |
| 2008/0270922 | A1 | 10/2008 | Kii et al. |
| 2009/0069642 | A1* | 3/2009 | Gao et al. .................. 600/300 |
| 2009/0324211 | A1 | 12/2009 | Strandell et al. |
| 2010/0234694 | A1 | 9/2010 | Takano et al. |
| 2011/0002223 | A1* | 1/2011 | Gross ......................... 370/235 |
| 2011/0023863 | A1 | 2/2011 | Andretich |
| 2011/0040574 | A1* | 2/2011 | Fung et al. .................. 705/2 |
| 2011/0231863 | A1 | 9/2011 | Takano et al. |

FOREIGN PATENT DOCUMENTS

| | | |
|---|---|---|
| JP | 2002-015068 | 1/2002 |
| JP | 2002-304201 | 10/2002 |
| JP | 2002-366653 | 12/2002 |
| JP | 2004-194174 | 7/2004 |
| JP | 2005-049199 | 2/2005 |
| JP | 2005-085871 | 3/2005 |
| JP | 2006-060438 | 3/2006 |
| JP | 2006-236176 | 9/2006 |
| JP | 2006-238237 | 9/2006 |
| JP | 2006-295823 | 10/2006 |
| JP | 2008-128927 | 5/2008 |
| JP | 2008-306464 | 12/2008 |
| WO | WO 03/017159 | 2/2003 |
| WO | WO 2006/018962 | 2/2006 |

OTHER PUBLICATIONS

Kurabayashi, Shuichi et al., "A Multidatabase System Architecture for Integrating Heterogeneous Databases with Meta-Level Active Rule Primitives," *Proceedings of the 20th IASTED International Conference on Applied Informatics*, 2002, 10 pages.

Notice of Rejection for JP 2009-060545 mailed Apr. 21, 2009 (with English translation), Translation Only.

Final Rejection for JP 2009-060545 mailed Sep. 15, 2009 (with English translation), Translation Only.

Decision of Rejection for JP 2009-545027 mailed Jun. 4, 2010 (with English translation).

Notice of Reasons for Rejection for JP 2009-545026 mailed Dec. 1, 2009 (with English translation).

Notice of Reasons for Rejection for JP 2009-545027 mailed Dec. 1, 2009 (with English translation).

Notice of Reasons for Rejection for JP 2009-545027 mailed Jun. 4, 2010 (with English translation).

Notice of Reasons for Rejection for JP 2009-545027, mailed Jun. 4, 2010 (with English translation).

International Preliminary Report on Patentability for PCT/JP2009/054139 mailed Oct. 27, 2011.

International Preliminary Report on Patentability for PCT/JP2009/054140 dated Oct. 28, 2011.

International Search Report and Written Opinion for PCT/JP2009/054139 mailed Apr. 28, 2009.

International Search Report and Written Opinion for PCT/JP2009/054140 mailed Apr. 28, 2009.

Non-final Office Action received for U.S. Appl. No. 12/665,107 dated Jul. 23, 2012.

Non-final Office Action received for U.S. Appl. No. 12/665,304 dated May 9, 2012.

Notice of Allowance received for U.S. Appl. No. 12/568,188 dated Jan. 4, 2011.

US Notice of Allowance on U.S. Appl. No. 12/665,304 DTD Sep. 18, 2012.

Non-Final Office Action for U.S. Appl. No. 12/665,107, mailed on Dec. 4, 2012, 15 pp.

Shin'ya and Takeo, M., "A Possibility of Estimation of the Degree of Interest by Eye Movement: Based on the interviews to the specialists of eyeball movement," downloaded from http://ci.nii.ac.jp/naid/110002556817, accessed on Jan. 21, 2013, 3 pp. (English Abstract only included).

Non-Final Office Action for U.S. Appl. No. 12/665,107, mailed on Apr. 22, 2013, 12 pp.

* cited by examiner

FIG. 6

| SERVICES | SENSORS FOR SERVICE AND THEIR PRIORITIES | | | | | | | | | | | | | | | SETS OF MODULES FOR SERVICES | PROPERTIES OF SERVICES |
|---|---|---|---|---|---|---|---|---|---|---|---|---|---|---|---|---|---|
| | 162 | 164 | 166 | 168 | 170 | 172 | 174 | 176 | 178 | 180 | 182 | 184 | 186 | 190-1 | 190-n | | |
| S#1 (HEALTH CHECK) | 0 | 3 | 1 | 0 | 0 | 2 | 0 | 0 | 0 | 0 | 0 | 0 | 0 | 0 | 0 | MS#1 | 2 |
| S#i (NAVIGATION) | 0 | 0 | 0 | 0 | 0 | 0 | 0 | 1 | 2 | 2 | 2 | 0 | 0 | 0 | 0 | MS#i | 1 |
| S#i+1 (IMAGE INFORMATION) | 0 | 0 | 0 | 0 | 0 | 0 | 0 | 1 | 2 | 2 | 2 | 0 | 0 | 0 | 0 | MS#i+1 | 4 |
| S#j | $N_{j1}$ | $N_{j2}$ | $N_{j3}$ | $N_{j4}$ | $N_{j5}$ | $N_{j6}$ | $N_{j7}$ | $N_{j8}$ | $N_{j9}$ | $N_{j10}$ | $N_{j11}$ | $N_{j12}$ | $N_{j13}$ | $N_{j14}$ | $N_{jk}$ | MS#j | 1 |
| S#n | $N_{n1}$ | $N_{n2}$ | $N_{n3}$ | $N_{n4}$ | $N_{n5}$ | $N_{n6}$ | $N_{n7}$ | $N_{n8}$ | $N_{n9}$ | $N_{n10}$ | $N_{n11}$ | $N_{n12}$ | $N_{n13}$ | $N_{n14}$ | $N_{nk}$ | MS#n | 3 |

FIG. 7

| SERVICES | PARAMETERS FOR MODULES ||||||||
|---|---|---|---|---|---|---|---|---|
| | #1 | #2 | ... | #i | #(i+1) | #(i+2) | #(i+3) | ... | #n |
| S#1 (HEALTH CHECK) | P'₁₁ | P'₁₂ | | - | - | - | - | | - |
| ... | | | | | | | | | |
| S#i (NAVIGATION) | - | - | | P'ᵢⱼ | P'ᵢ(ⱼ₊₁) | P'ᵢ(ⱼ₊₂) | | | - |
| S#i+1 (IMAGE INFORMATION) | - | - | | P'ᵢⱼ | P'ᵢ(ⱼ₊₁) | | P'ᵢ(ⱼ₊₃) | | - |
| ... | | | | | | | | | |
| S#n | P'ₙ₁ | P'ₙ₂ | | P'ₙⱼ | P'ₙ(ⱼ₊₁) | P'ₙ(ⱼ₊₂) | | | P'ₙₙ |

FIG. 8

| SERVICES | PARAMETERS FOR SENSORS | | | | | | | | | | | | | | | |
|---|---|---|---|---|---|---|---|---|---|---|---|---|---|---|---|---|
| | 160 | 162 | 166 | 168 | 170 | 172 | 174 | 176 | 178 | 180 | 182 | 184 | 186 | 190-1 | | 190-n |
| S#1 (HEALTH CHECK) | - | $P_{12}$ | $P_{13}$ | - | - | $P_{16}$ | - | - | - | - | - | - | - | - | | - |
| S#i (NAVIGATION) | - | - | - | - | - | - | - | $P_{i8}$ | $P_{i9}$ | $P_{i10}$ | $P_{i11}$ | $P_{i12}$ | - | - | | - |
| S#i+1 (IMAGE INFORMATION) | - | - | - | - | - | - | - | $P_{i8}$ | $P_{i9}$ | $P_{i10}$ | $P_{i11}$ | $P_{i12}$ | - | - | | - |
| S#j | $P_{j1}$ | $P_{j2}$ | $P_{j3}$ | $P_{j4}$ | $P_{j5}$ | $P_{j6}$ | $P_{j7}$ | $P_{j8}$ | $P_{j9}$ | $P_{j10}$ | $P_{j11}$ | $P_{j12}$ | $P_{j13}$ | $P_{j14}$ | | $P_{jk}$ |
| S#n | $P_{n1}$ | $P_{n2}$ | $P_{n3}$ | $P_{n4}$ | $P_{n5}$ | $P_{n6}$ | $P_{n7}$ | $P_{n8}$ | $P_{n9}$ | $P_{n10}$ | $P_{n11}$ | $P_{n12}$ | $P_{n13}$ | $P_{n14}$ | | $P_{nk}$ |

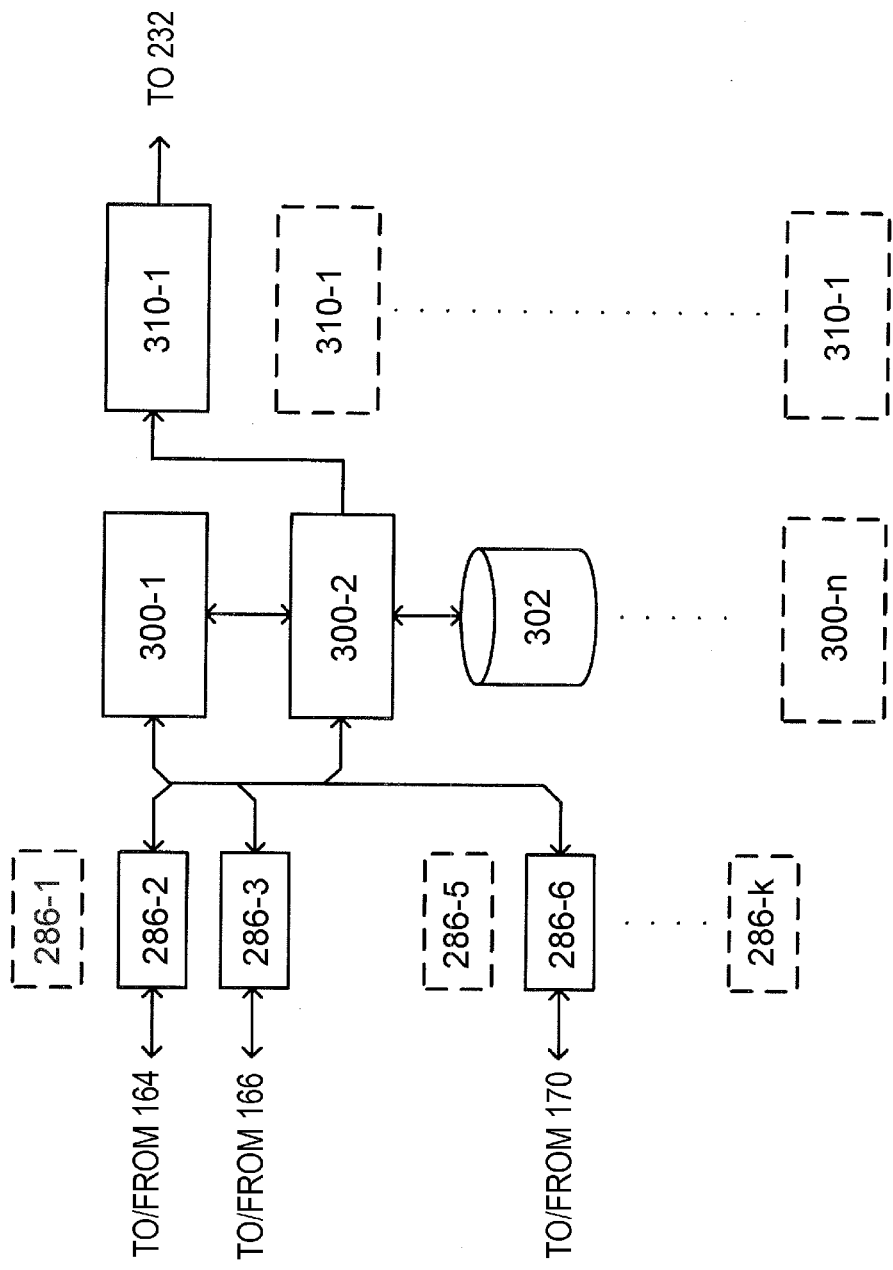

FIG. 15

| SERVICES | SENSORS FOR SERVICE AND THEIR PRIORITIES | | | | | | | | | | | | | | | SETS OF MODULES FOR SERVICES | PROPERTIES OF SERVICES |
|---|---|---|---|---|---|---|---|---|---|---|---|---|---|---|---|---|---|
| | 162 | 164 | 166 | 168 | 170 | 172 | 174 | 176 | 178 | 180 | 182 | 184 | 186 | 190-1 | 190-n | | |
| S#1 (HEALTH CHECK) | 0 | 3 | 1 | 0 | 0 | 2 | 0 | 0 | 0 | 0 | 0 | 0 | 0 | 0 | 0 | MS#1 | 2 |
| S#i (NAVIGATION) | 0 | 0 | 0 | 0 | 0 | 0 | 0 | 1 | 2 | 2 | 2 | 0 | 0 | 0 | 0 | MS#i | 1 |
| S#i+1 (IMAGE INFORMATION) | 0 | 0 | 0 | 0 | 0 | 0 | 0 | 1 | 2 | 2 | 2 | 0 | 0 | 0 | 0 | MS#i+1 | 1 |
| S#m (WEB BROWSER) | 1/2 | 1/2 | 0 | 1 | 0 | 0 | 0 | 0 | 0 | 0 | 0 | 0 | 1 | 0 | 0 | MS#j | 1 |
| S#n | $N_{n1}$ | $N_{n2}$ | $N_{n3}$ | $N_{n4}$ | $N_{n5}$ | $N_{n6}$ | $N_{n7}$ | $N_{n8}$ | $N_{n9}$ | $N_{n10}$ | $N_{n11}$ | $N_{n12}$ | $N_{n13}$ | $N_{n14}$ | $N_{nk}$ | MS#n | 3 |

FIG. 16

| SERVICES | PARAMETERS FOR SENSORS | | | | | | | | | | | | | | | | |
|---|---|---|---|---|---|---|---|---|---|---|---|---|---|---|---|---|---|
| | 160 | 162 | 166 | 168 | 170 | 172 | 174 | 176 | 178 | 180 | 182 | 184 | 186 | 190-1 | | | 190-n |
| S#1 (HEALTH CHECK) | - | $P_{12}$ | $P_{13}$ | - | - | $P_{16}$ | - | - | - | - | - | - | - | - | | | - |
| S#i (NAVIGATION) | - | - | - | - | - | - | - | $P_{i8}$ | $P_{i9}$ | $P_{i10}$ | $P_{i11}$ | $P_{i12}$ | - | - | | | - |
| S#i+1 (IMAGE INFORMATION) | - | - | - | - | - | - | - | $P_{i8}$ | $P_{i9}$ | $P_{i10}$ | $P_{i11}$ | $P_{i12}$ | - | - | | | - |
| S#m (WEB BROWSER) | $P_{m1}$ | $P_{m2}$ | - | $P_{m4}$ | - | - | - | - | - | - | - | - | $P_{m13}$ | - | | | - |
| S#n | $P_{n1}$ | $P_{n2}$ | $P_{n3}$ | $P_{n4}$ | $P_{n5}$ | $P_{n6}$ | $P_{n7}$ | $P_{n8}$ | $P_{n9}$ | $P_{n10}$ | $P_{n11}$ | $P_{n12}$ | $P_{n13}$ | $P_{n14}$ | | | $P_{nk}$ |

FIG. 17

| SERVICES | PARAMETERS FOR MODULES | | | | | | | | | | | |
|---|---|---|---|---|---|---|---|---|---|---|---|---|
| | #1 | #2 | ... | #i | #(i+1) | #(i+2) | #(i+3) | ... | #p | #(p+1) | #(p+2) | ... | #n |
| S#1 (HEALTH CHECK) | P'$_{11}$ | P'$_{12}$ | | - | - | - | - | | | | | | |
| ... | | | | | | | | | | | | | |
| S#i (NAVIGATION) | - | - | | P'$_{ij}$ | P'$_{i(j+1)}$ | P'$_{i(j+2)}$ | - | | | | | | - |
| S#i+1 (IMAGE INFORMATION) | - | - | | P'$_{ij}$ | P'$_{i(j+1)}$ | - | P'$_{(i+1)(j+3)}$ | | | | | | - |
| ... | | | | | | | | | | | | | |
| S#m (WEB BROWSER) | - | - | | | | | | | P'$_{mp}$ | P'$_{m(p+1)}$ | P'$_{m(p+2)}$ | | P'$_{mn}$ |
| ... | | | | | | | | | | | | | |
| S#n | P'$_{n1}$ | P'$_{n2}$ | | P'$_{nj}$ | P'$_{n(j+1)}$ | P'$_{n(j+2)}$ | - | | | | | | P'$_{nn}$ |

HEALTH CHECK SYSTEM, HEALTH CHECK APPARATUS AND METHOD THEREOF

BACKGROUND OF THE INVENTION

1. Field of the Invention

The present invention relates to a health check system, a health check apparatus and a method thereof for providing information on a user's health using a sensor.

2. Description of the Related Art

For example, Shuichi Kurabayashi, Naoki Ishibashi, Yasuo Kiyoki: "Scheme for Realizing Active Type Multidatabase System in Mobile Computing Environment," Proceedings of Information Processing Society of Japan, 2000-DBS-122, 2000, 463-470 and Shuichi Kurabayashi, Naoki Ishibashi, Yasushi Kiyoki: A Multidatabase System Architecture for Integrating Heterogeneous Databases with Meta-Level Active Rule Primitives. In Proceedings of the 20th TASTED International Conference on Applied Informatics, 2002, 378-387, disclose an active meta-level system that dynamically interconnects devices of databases or the like.

However, these documents neither disclose nor even suggest any health check system, health check apparatus or method thereof for providing information on a user's health by adaptively using sensors.

SUMMARY OF THE INVENTION

The health check apparatus disclosed in the present application is configured to include one or more sensor drive modules, one or more service execution modules, an input device that receives an input specifying one or a plurality of health check services, a selector that selects the one or more sensor drive modules and the one or more service execution modules necessary to realize the one or more specified health check services based on association information that associates the plurality of health check services with the one or more sensor drive modules necessary for realization thereof and the one or more service execution modules, a plurality of types of physiological sensors that match any one of the sensor drive modules and detect physiological information from health check targets according to the types thereof, an execution device that executes the selected sensor drive modules and the service execution modules, delivers information inputted/outputted between the modules so as to match the realization of the specified health check service and realizes the specified health check service, and an output device that outputs one or more results of the realized health check service, wherein the executed sensor drive module drives the matching physiological sensor, detects physiological information of the health check target corresponding to the type of the physiological sensor and outputs the information as physiological sensor information and the respective service execution modules executed process physiological sensor information outputted from the executed sensor drive module and output the processing result to the output device as a result of the specified health check service.

Here, a summary of disclosed particulars of the present application will be explained.

However, the explanations here are intended to help understand the disclosed particulars of the present application, but not intended to limit the technical scope thereof.

The health check apparatus disclosed in the present application is a hybrid combination of different types of sensor functions configured to be able to detect a user's context (situation) and is also called, for example, a "hybrid sensing system."

The health check apparatus disclosed in the present application is provided with a plurality of types of sensors that measure physiological information (perspiration, pulsation, blood pressure, brain waves, signal generated by the heart and blood components such as blood glucose level and neutral fat value) of a user—a health check target.

Furthermore, it is necessary to use different types of sensors to conduct various types of information health checks.

Furthermore, to keep quality as high as possible in an identical health check, different sensors need to be used depending on conditions.

For example, when a simple health check is provided as an information service, it may be necessary to change sensor settings such as sensitivity of a blood pressure sensor and a pulsation sensor from one user to another, who is the simple health check target.

Furthermore, when an attempt is made to output comments on the health based on output signals of the sensors for the user in the processing of realizing the simple health check, it may be necessary to change settings on the processing such as blood pressure and pulsation in daily life conditions from one user to another.

The health check apparatus disclosed in the present application is devised from the above described standpoint and is configured so as to select sensors available to realize a health check to be provided from among the plurality of sensors available to the apparatus and select any one of optimal sensors from among the sensors available.

Furthermore, the health check apparatus disclosed in the present application is configured so as to appropriately provide a health check, select appropriate parameters and set the parameters.

Furthermore, the health check apparatus disclosed in the present application is configured to only receive the user's specification of a desired information service, appropriately combine various types of sensors and a plurality of processing programs so as to be able to provide a variety of health checks.

Technical advantages disclosed in the present application and other technical advantages will be made clear for those skilled in the art by reading detailed descriptions of embodiments illustrated in the accompanying drawings.

The accompanying drawings are integrated in the specification of the present application to form a part thereof, illustrate the embodiments of the present application and play the role of describing principles disclosed in the present application as well as describing the embodiments.

The drawings referred to in the specification of the present application should be interpreted not to have been drawn on a fixed scale unless specified otherwise.

BRIEF DESCRIPTION OF THE DRAWINGS

FIG. 6 is a first diagram illustrating a first service definition table stored in the input analysis DB shown in FIG. 4;

FIG. 7 is a first diagram illustrating a service execution parameter table stored in the parameter DB shown in FIG. 4;

FIG. 8 is a first diagram illustrating a sensor parameter table stored in the parameter DB shown in FIG. 4;

FIG. 12 illustrates a first information service (health check) delivered by the mobile stations and fixed terminals shown in FIG. 1;

FIG. 15 is a second diagram illustrating a service definition table stored in the input analysis DB shown in FIG. 4;

FIG. 16 is a second diagram illustrating a sensor parameter table stored in the parameter DB shown in FIG. 4;

FIG. 17 is a second diagram illustrating a service execution parameter table stored in the parameter DB shown in FIG. 4;

DETAILED DESCRIPTION OF THE PREFERRED EMBODIMENTS

First Embodiment

Hereinafter, a first embodiment disclosed in the present application will be explained in detail.

The embodiments disclosed in the present application are illustrated in the accompanying drawings.

Although the disclosure of the present application will be explained in association with the embodiments, it will be understood by those skilled in the art that the present embodiments are not intended to limit the disclosure of the present application to the disclosed contents.

By contrast, the disclosure of the present application is intended to include the spirit of the disclosure of the present application, and alternatives, modifications and equivalents that can be included in the disclosure of the present application.

Furthermore, the disclosure of the present application will be explained specifically and in detail so that the disclosure of the present application can be sufficiently understood.

However, as is obvious for those skilled in the art, the disclosure of the present application is not meant to be implemented only by using all the particulars described specifically and in detail.

Known methods, procedures, components and circuits may not be described in detail so as to prevent aspects of the present disclosure from being unnecessarily hard to understand.

However, what should be noted is that all these and similar terms should be associated with appropriate physical quantities and the terms are merely expedient labels associated with these quantities.

As will be obvious from the following discussions, the discussions using terms such as "receive," "deliver" and "setting" throughout the entire disclosure of the present application will be understood to refer to actions and processes of an electronic computing device such as a computer system unless specified otherwise.

The electronic computing device such as a computer system operates data expressed as physical (electronic) quantities in a register and memory of the computer system and converts the data to other data likewise expressed as physical quantities in a computer system memory or register or other information storage, transmission or display device.

Furthermore, the disclosure of the present application is also suitable for use in other computer systems, for example, optical and mechanical computers.

[Information Service Delivery System 1]

Hereinafter, an information service delivery system 1 to which the disclosed particulars of the present application are applied will be explained.

Figure 1:
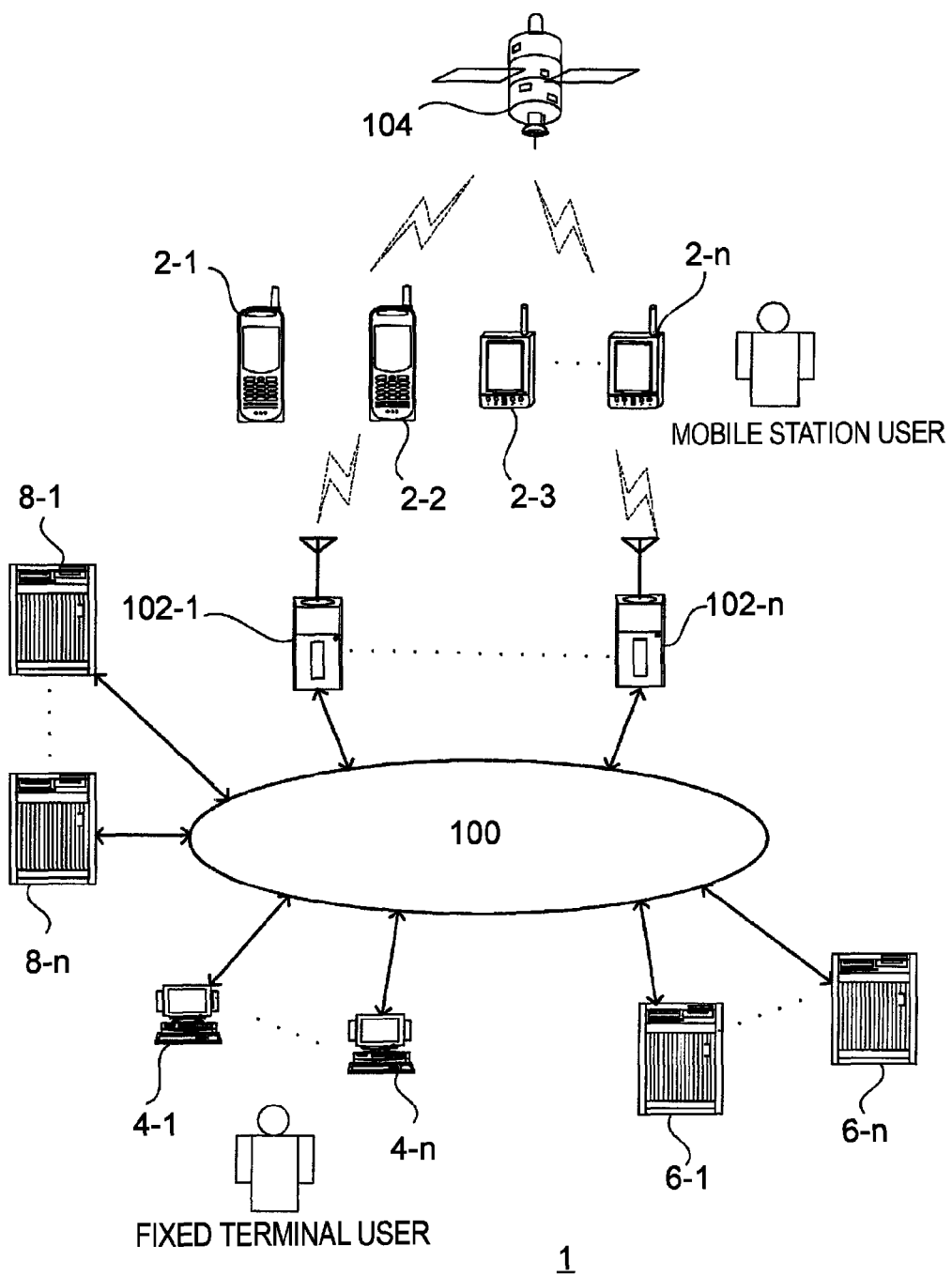
FIG. 1 illustrates a configuration of an information service delivery system to which disclosed particulars of the present application are applied.

FIG. 1 illustrates a configuration of the information service delivery system 1 to which the disclosed particulars of the present application are applied.

The information service delivery system 1 is configured by connecting mobile stations 2-1 to 2-$n$, fixed terminals 4-1 to 4-$n$, base stations 102-1 to 102-$n$, module/parameter server apparatuses 6-1 to 6-$n$ and Web servers 8-1 to 8-$n$ via a network 100 applicable to both wired and wireless communications.

Furthermore, the mobile stations 2-1 to 2-$n$ can receive radio wave signals for positioning from a GPS artificial satellite 104 at locations suitable for receiving radio wave such as outdoors.

In the information service delivery system 1, the mobile stations 2-1 to 2-$n$ are, for example, mobile phones, PDAs (Personal Digital Assistants) capable of radio communication, digital cameras and portable type personal computers.

The fixed terminals 4-1 to 4-$n$ are, for example, desktop computers.

Furthermore, the base stations 102-1 to 102-$n$ carry out data transmission to/from the fixed terminals 4-1 to 4-$n$ and mobile stations 2-1 to 2-$n$ via radio channels.

The Web servers 8-1 to 8-$n$ return Web data at the request of the mobile stations 2/fixed terminals 4.

Furthermore, the mobile stations 2-1 to 2-$n$ can receive radio wave signals for positioning from the GPS artificial satellite 104 at locations suitable for receiving radio waves such as outdoors.

$n$ denotes an integer equal to or greater than 1, and $i$ and $j$ denotes integers that satisfy $i \leq i, j \leq n$, but these symbols $i$, $j$ and $n$ do not always denote the same numbers.

Furthermore, when one or more of a plurality of components such as the mobile stations 2-1 to 2-$n$ are indicated without particularly specifying the number of such components, abbreviation such as "mobile station 2" may be used.

Furthermore, components that can be entities of information communication and information processing such as the base station 102, mobile station 2, fixed terminal 4 and module/parameter server apparatus 6 may be collectively called "nodes."

Furthermore, substantially the same components and processing in the respective drawings will be assigned the same reference numerals below unless specified otherwise.

The information service delivery system 1 uses these components to realize information processing through nodes and information communication among the nodes, and further functions as the aforementioned hybrid sensing system.

[Hardware Configuration]

Hereinafter, a hardware configuration of each node of the information service delivery system 1 will be explained.

Figure 2:
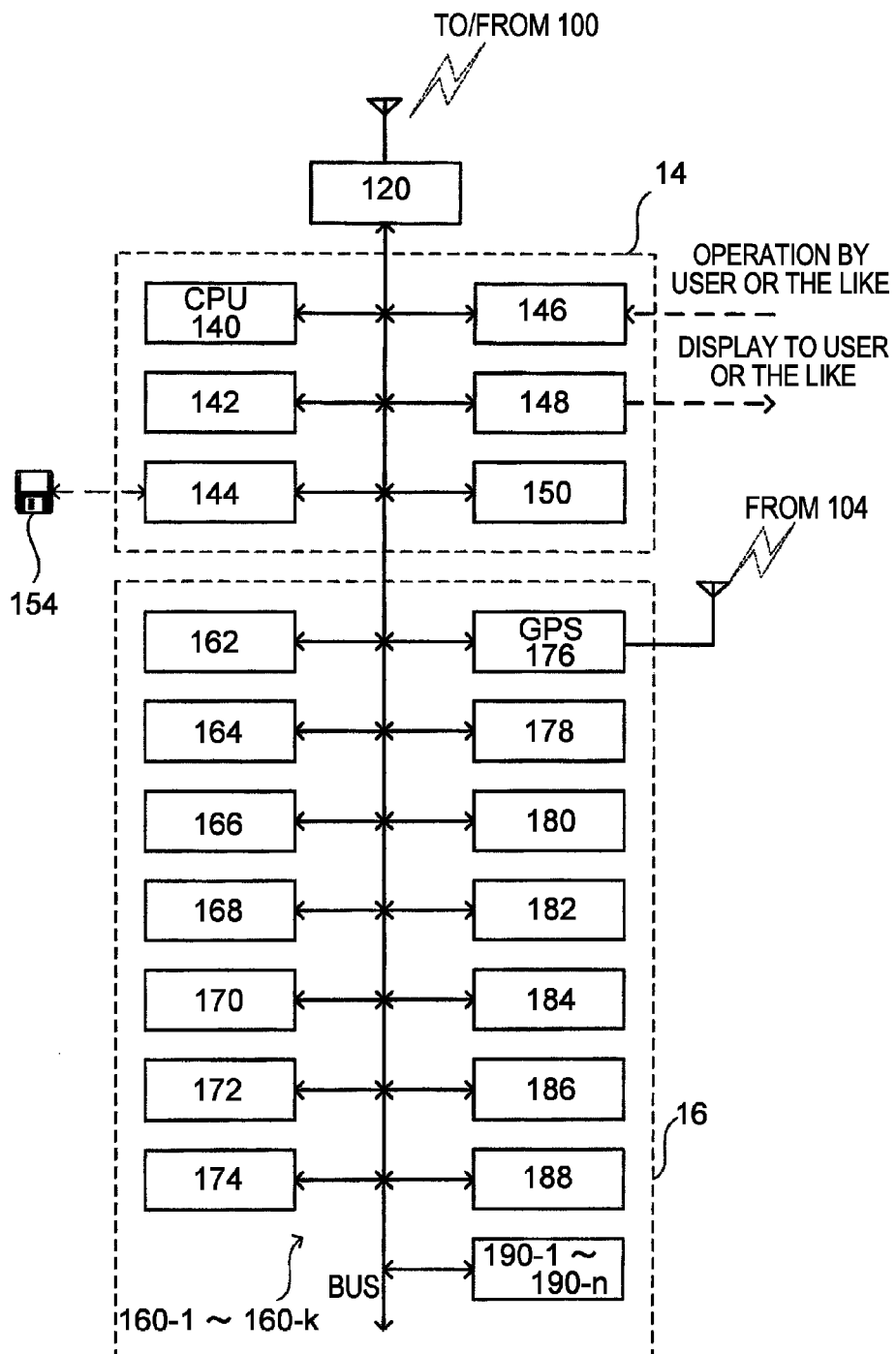
FIG. 2 illustrates a hardware configuration of the mobile stations and fixed terminal shown in FIG. 1.

FIG. 2 illustrates a hardware configuration of the mobile station 2 or fixed the terminal 4 shown in FIG. 1.

As shown in FIG. 2, the mobile station 2 or fixed terminal 4 is configured by connecting a communication apparatus 120 connected to a network 100 via a wireless communication channel or wired communication channel, a data processing section 14 and a sensor section 16 via a bus.

The data processing section 14 is made up of a CPU 140, a memory 142, a CPU peripheral apparatus 144 such as an interrupt control device, a timer device and a recording medium interface that reads/writes data from/to a recording medium 154, an input device 146 such as input buttons such as a numerical keypad and a microphone, an output device 148 such as a liquid crystal display apparatus and a speaker and a camera 150 that can take moving images and still images and output the images taken as image data in digital format.

The sensor section 16 includes, for example, a perspiration sensor 162, a pulsation sensor 164, a blood pressure sensor 166, a brain wave sensor 168, a heart signal sensor 170, a body temperature sensor 172, a blood component sensor 174, a GPS 176, a direction sensor 178, an acceleration sensor 180, a speed sensor 182, a temperature/humidity sensor 184, a viewpoint detection sensor 186, a pedometer 188 and other sensors 190-1 to 190-*n* such as sensors to use an RF-ID sensor (hereinafter, these sensors are collectively called "sensors 160-1 to 160-*k*" (k is the number of sensors included in the sensor section 16)).

That is, the mobile station 2 or fixed terminal 4 includes components as a general computer capable of detecting information from sensors and carrying out information processing and information communication.

FIG. 2 shows a case where the sensor section 16 includes a plurality of types of sensors 160, one sensor per type, as a specific example, but the sensor section 16 may also include a plurality of types of sensors 160, a plurality of sensors per type.

The respective sensors above included in the sensor section 16 are driven and controlled by their respective matching device driver programs, detect information corresponding to the respective types and output the information as sensor information.

In the sensor section 16, the perspiration sensor 162 detects the amount of perspiration of the user of the mobile station 2 or fixed terminal 4 (mobile station user, fixed terminal user).

The pulsation sensor 164 detects pulsation of the user of the mobile station 2 or the like.

The blood pressure sensor 166 detects a blood pressure of the user of the mobile station 2 or the like.

The brain wave sensor 168 detects brain waves of the user of the mobile station 2 or the like.

The heart signal sensor 170 detects an electric signal produced by the heart of the user of the mobile station 2 or the like.

The body temperature sensor 172 detects a body temperature of the user of the mobile station 2 or the like.

The blood component sensor 174 detects the amount of blood components such as the amount of blood sugar, amount of neutral fat in the blood and uric acid value in the blood.

The GPS 176 detects the position (latitude, longitude) of the mobile station 2 or the like using a radio wave signal from a GPS artificial satellite 104 (FIG. 1).

The direction sensor 178 detects the moving direction of the mobile station 2 or the like using a compass, gyro or the like.

The acceleration sensor 180 detects acceleration given to the mobile station 2 or the like.

The speed sensor 182 detects the moving speed of the mobile station 2 or the like.

The temperature/humidity sensor 184 detects the temperature/humidity of outside air.

The viewpoint detection sensor 186 photographs the face of the user of the mobile station 2 or the like and detects the user's viewpoint.

The pedometer 188 detects the number of steps of the user of the mobile station 2 or the like.

Figure 3:
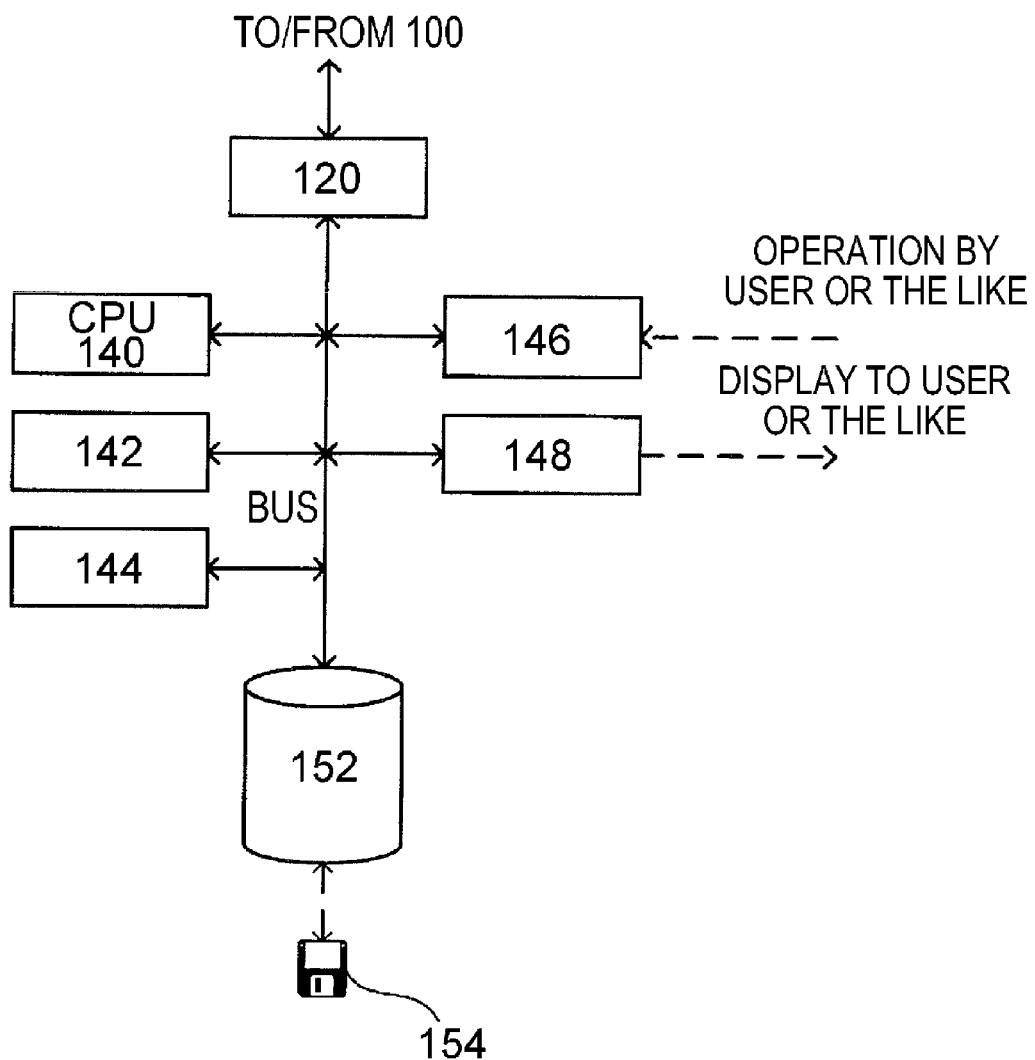
FIG. 3 illustrates a hardware configuration of the server apparatus shown in FIG. 1.

FIG. 3 illustrates a hardware configuration of the module/parameter server apparatus 6 shown in FIG. 1.

As shown in FIG. 3, the module/parameter server apparatus 6 is made up of a communication apparatus 120, a CPU 140, a memory 142, a CPU peripheral apparatus 144, an input device 146, an output device 148 and a recording apparatus 152 such as an HDD/CD apparatus.

That is, the module/parameter server apparatus 6 includes components as a general computer capable of information processing and information communication.

[Software]

Hereinafter, the software (program) executed at each node of the information service delivery system 1 will be explained.

[Terminal Program 20]

First, a terminal program 20 which is executed in the mobile station 2 or fixed terminal 4 will be explained.

Figure 4:
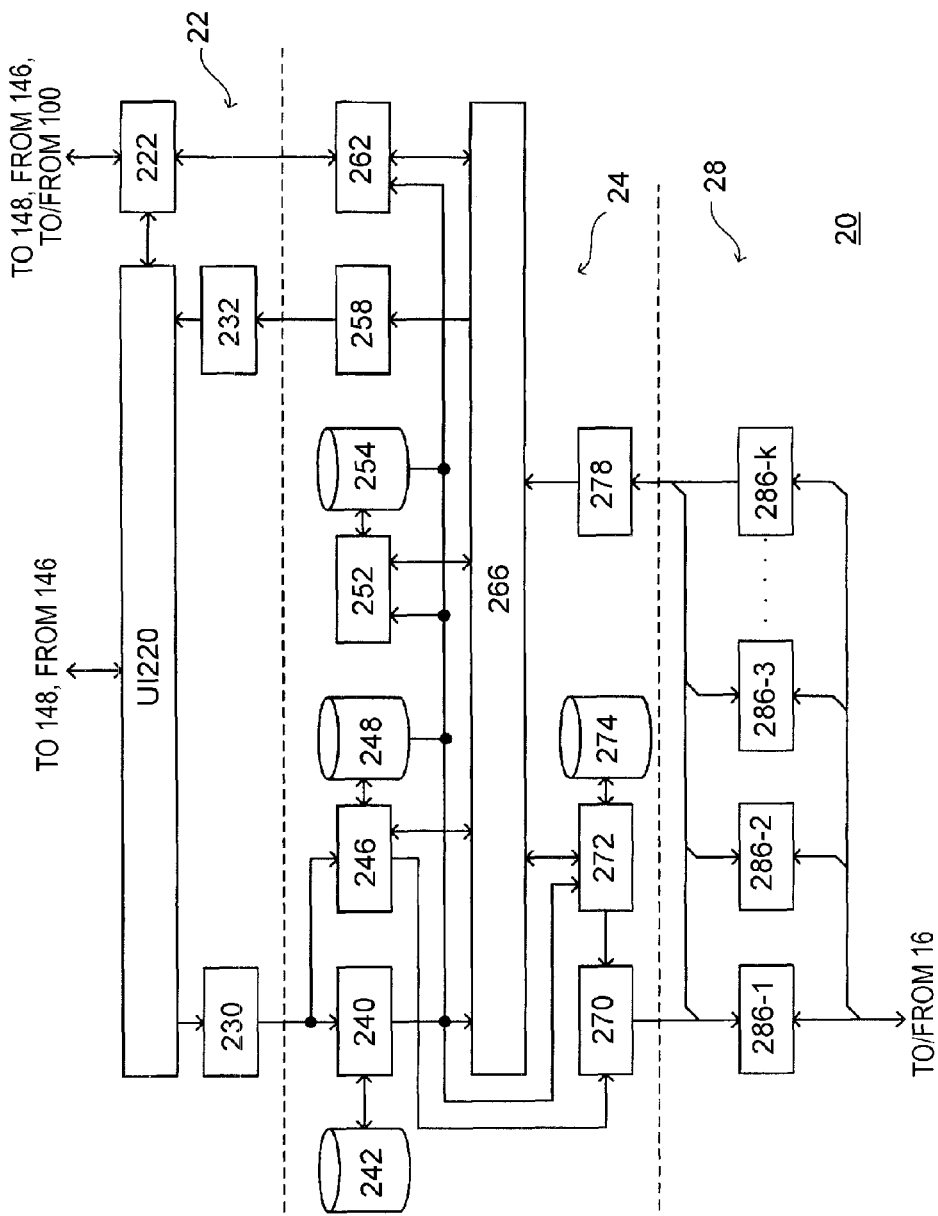
FIG. 4 illustrates a terminal program executed by the mobile stations and fixed terminals shown in FIG. 1 and FIG. 2.

FIG. 4 illustrates the terminal program 20 executed in the mobile station 2 or fixed terminal 4 shown in FIG. 1 and FIG. 2.

As shown in FIG. 4, the terminal program 20 is made up of a service delivery section 22, middleware 24 and a sensor drive section 28.

The service delivery section 22 is made up of a user interface section (UI) 220, a communication processing section 222, an application input section 230 and an information output section 232.

The middleware 24 is made up of an input analysis section 240, an input analysis database (DB) 242, a parameter setting section 246, a parameter DB 248, a module selection section 252, a module DB 254, an information generation section 258, an information acquisition section 262, a module execution control section 266, a sensor control section 270, a sensor selection section 272, a sensor drive module DB 274 and a sensor output processing section 278.

The sensor drive section 28 is made up of sensor drive modules 286-1 to 286-*k*.

The terminal program 20 is loaded into the memory 142 of the mobile station 2 or fixed terminal 4 via the recording medium 154 (FIG. 2, FIG. 3) and network 100 or the like and executed by specifically using hardware resources of the mobile station 2 or fixed terminal 4 on an OS (not shown)

executed by the mobile station 2 or fixed terminal (the same applies to the following programs and modules).

The terminal program 20 receives the user's specification of a desired information service through these components, selects a sensor 160, a sensor drive module 286, a service execution module 300 and an information creation module 310 (which will be described later with reference to FIG. 5) necessary to realize the specified information service, combines these components and realizes the specified information service.

When a plurality of information services are specified, the terminal program 20 realizes the plurality of information services simultaneously in parallel.

[Service Delivery Section 22]

In the service delivery section 22 of the terminal program 20, the UI 220 displays a GUI (Graphic User Interface) image (not shown) that prompts the user to select an information service on a display apparatus of the output device 148.

Furthermore, the UI 220 receives an operation by the user of specifying a desired information service from the input device 146 according to the displayed GUI image and outputs information for specifying the specified information service to the application input section 230.

Furthermore, the UI 220 outputs a voice signal inputted from a microphone of the input device 146 to the communication processing section 222 and outputs the voice signal inputted from the communication processing section 222 to a speaker of the output device 148.

The communication processing section 222 performs processing for voice communication and general information communication in the mobile station 2 or fixed terminal 4 and processing for information communication with the module/parameter server apparatus 6 via the network 100.

The application input section 230 receives information for specifying the information service inputted from the UI 220 and outputs the information to the middleware 24.

The information output section 232 receives the results of specified information services from the middleware 24 and outputs an image and voice or the like via the UI 220 in a format predetermined for each specified service.

[Sensor Drive Module, Service Execution Module, Information Creation Module]

In order to help understand the middleware 24, the sensor drive module 286, the service execution module 300 and the information creation module 310 (these are collectively called "modules") will be explained before the explanation of the middleware 24.

Figure 5:
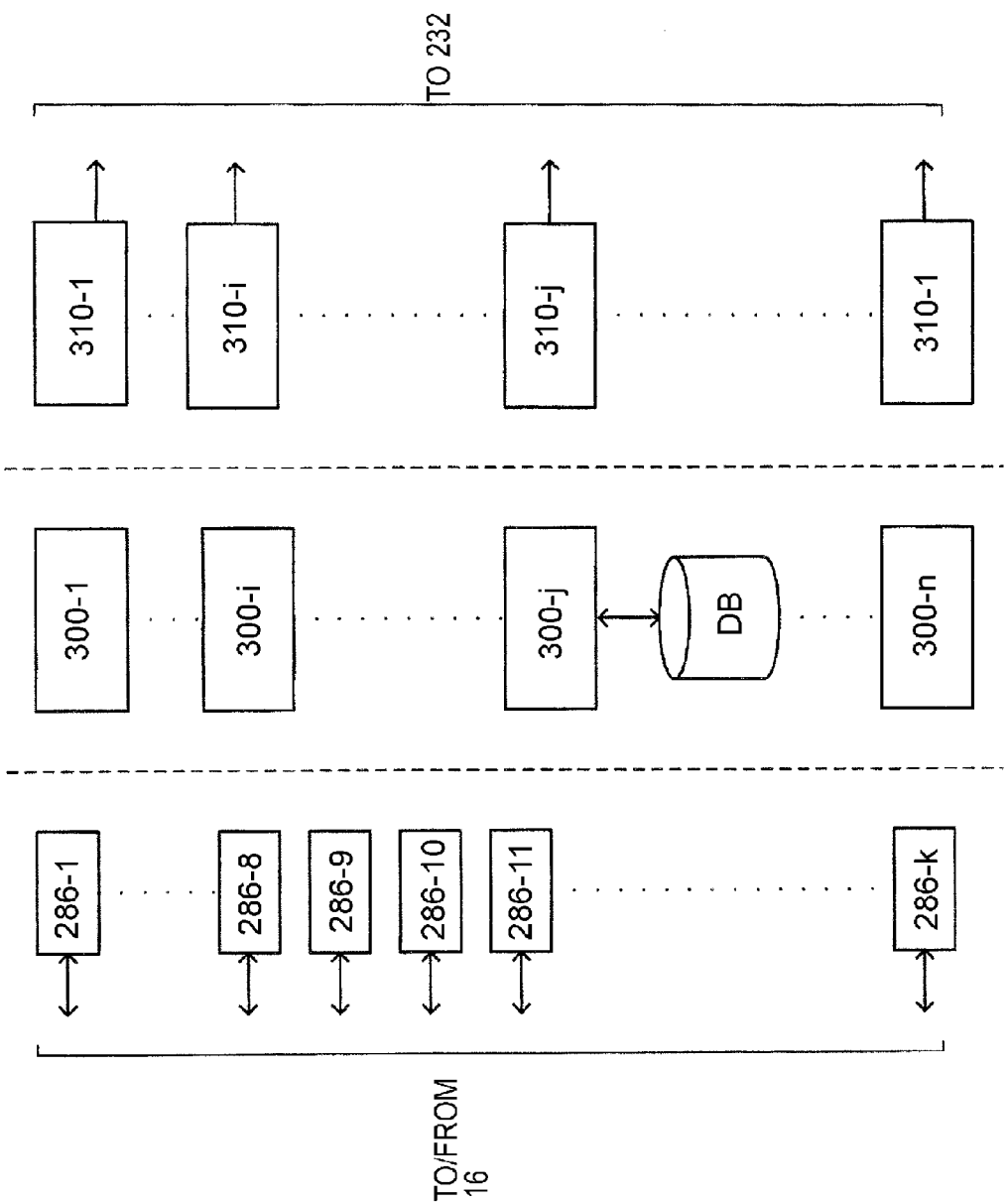
FIG. 5 illustrates sensor drive modules, service execution modules and information creation modules executed by the terminal program shown in FIG. 4.

FIG. 5 illustrates the sensor drive module 286, service execution module 300 and information creation module 310 executed by the terminal program 20 shown in FIG. 4.

These modules are executed according to the control of the middleware 24.

The sensor drive modules 286-1 to 286-$k$ correspond to the sensors 160-1 to 160-$k$ respectively and match the corresponding sensors 160.

That is, the sensor drive module 286 corresponding to the sensor 160 selected to realize the information service specified by the user receives a setting of a sensor parameter (P; which will be described later with reference to FIG. 8) for optimally operating the corresponding sensor 160 and causes the sensor 160 to operate using the set sensor parameter P.

The sensor drive module 286 further generates sensor information indicating information on the temperature/position (latitude/longitude) or the like detected by the corresponding sensor 160 and outputs the sensor information to the service execution module 300 selected to realize the information service specified by the user.

The selected service execution module 300 receives a setting of a service execution parameter (P'; which will be described later with reference to FIG. 7) for optimally executing the selected processing.

Furthermore, the service execution module 300 receives sensor information from the sensor drive module 286 corresponding to one or more selected sensors 160, processes the received sensor information using the set service execution parameter P' and thereby executes the specified information service.

The selected service execution module 300 outputs the processing result of the information service to the information creation module 310 selected to realize the information service specified by the user.

The selected information creation module 310 receives the setting of an information creation parameter P' (e.g., output format of the result of information processing service) for optimally executing the selected processing.

Furthermore, the information creation module 310 receives the processing results of one or more selected service execution modules 300, processes the received sensor processing results using the set information creation parameter P', thereby creates a result of the information processing service that matches a format predetermined for each information processing service (voice, image format or the like) and outputs the result of the information processing service to the information output section 232 of the service delivery section 22.

[Middleware 24/Sensor Drive Section 28]

FIG. 6 is a first diagram illustrating a first service definition table stored in the input analysis DB 242 shown in FIG. 4.

In the middleware 24, the input analysis DB 242 stores the service definition table shown in FIG. 6 so that the service definition table may be referred to by the input analysis section 240.

The input analysis section 240 refers to the service definition table stored in the input analysis DB 242 and reports the module corresponding to the specified information service to the module execution control section 266, module selection section 252, information acquisition section 262 and sensor selection section 272.

The information acquisition section 262 refers to the parameter DB 248 and module DB 254, judges whether or not there exist the module, sensor parameter P, service execution parameter P' and information creation parameter P' (these are collectively called "modules and parameters") considered necessary to realize the information service judged executable by the module execution control section 266 out of the specified information services in the reporting from the input analysis section 240.

When any one or more modules and parameters considered necessary to realize the specified information service do not exist, the information acquisition section 262 requests the one or more modules and parameters which do not exist in the mobile station 2 or fixed terminal 4 from the module/parameter server apparatus 6 (FIG. 1) via the network 100.

The information acquisition section 262 causes the module DB 254 to store the one or more modules returned from the module/parameter server apparatus 6 in response to this request and also causes the parameter DB 248 to store any one or more of the sensor parameter P, service execution parameter P' and information creation parameter P' (these are collectively called "parameters") returned from the module/parameter server apparatus 6.

Furthermore, a combination (MS#1 to MS#n) of one or more service execution modules 300 and one or more information creation modules 310 used in the respective information services includes information for defining the sensor 160 (sensor drive module 286) from which the service execution module 300 receives sensor information.

Furthermore, this combination (MS#1 to MS#n) includes information for defining what kind of information is inputted/outputted between a certain service execution module 300 and any one of the other service execution modules 300, and which service execution module 300 outputs a processing result to which information creation module 310.

Furthermore, the combination (MS#1 to MS#n) shows information for defining what kind of information is inputted/outputted between a certain information creation module 310 and any one of the other information creation modules 310, and which information creation module 310 outputs a result of a final information service to the information generation section 258.

The priority of the sensor 160 indicates which sensor 160 (sensor drive module 286) should be used when a plurality of sensors 160 are available in a specified one information service.

As described above, FIG. 6 illustrates that when the mobile station 2 or fixed terminal 4 delivers a navigation service as the information service, the service execution module 300 processes the sensor information (latitude/longitude) of the GPS 176 when the GPS 176 (FIG. 2) can receive a radio wave signal from the GPS artificial satellite 104 (FIG. 1), whereas when the GPS 176 cannot receive the radio wave signal, the service execution module 300 should calculate position information through integral processing using the sensor information outputted by the direction sensor 178, acceleration sensor 180 and speed.

The priority of the information service is indicated by a numerical value such as 1, 2, 3, . . . or the like as with the priority of the sensor 160, indicating that the smaller the numerical value, the higher is the priority.

When, for example, a plurality of information services are specified and the plurality of information services require the same resources or when all the information services cannot be executed due to a limit of the processing capacity of the data processing section 14 (FIG. 2) of the mobile station 2 or fixed terminal 4 or the like, the priority of the information service indicates which information service(s) should be executed with higher priority.

That is, when all of the plurality of information services using the same sensor 160 cannot be executed, information services with higher priority are executed first.

Furthermore, when all of the plurality of information services cannot be executed due to a limit of the processing capacity of the data processing section 14, the information services are executed in descending order of priority and information services with low priority whose execution might cause the processing capacity of the data processing section 14 to reach the limit are not executed.

Furthermore, when, for example, an information service is specified, the priority of the information service indicates which combination of sensors 160 should be executed with high priority when sensors that can provide sensor data necessary to improve the accuracy, response speed and details or the like of the information service are not available.

For example, the priority of an information service indicates that an optimal result is obtained when one blood pressure sensor 166, one pulsation sensor 164 and two brain wave sensors 169 are available in a health check service, whereas when only one blood pressure sensor 166 and pulsation sensor 164 are available, this health check service can be executed using these two sensors 160.

FIG. 7 is a first diagram illustrating a service execution parameter table stored in the parameter DB 248 shown in FIG. 4.

FIG. 8 is a first diagram illustrating a sensor parameter table stored in the parameter DB 248 shown in FIG. 4.

The parameter DB 248 stores the service execution parameter table shown in FIG. 7, the sensor parameter table shown in FIG. 8 and an information creation parameter table having a configuration similar to that of the service execution parameter table shown in FIG. 7 so as to be referred to from the parameter setting section 246 and information acquisition section 262.

The parameter setting section 246 refers to the sensor parameter table, service execution parameter table and information creation parameter table stored in the parameter DB 248 and outputs the sensor parameter P of the sensors 160 (sensor drive module 286) considered necessary to realize the information services judged to be realizable by the module execution control section 266 out of the specified services to the sensor control section 270.

Furthermore, the parameter setting section 246 outputs the service execution parameter P' and information creation parameter P' of the service execution module 300 and information creation module 310 considered necessary to realize the specified service to the module execution control section 266.

Hereinafter, the roles of the service definition table and sensor parameter table shown in FIG. 7 and FIG. 8 will be explained.

To realize the aforementioned hybrid sensing system, the service definition table and the sensor parameter table are used to describe a pattern of combinations of different sensors 160 according to the purpose of the user.

First, the service definition table (FIG. 7) will be explained.

The correspondence between a context to be extracted and a combination of the sensors 160 is set in the service definition table.

A set value in the service definition table indicates the number of sensors used, and a numerical value 0 indicates that the sensor 160 to which this numerical value is assigned is not available.

Furthermore, the service definition table can describe a plurality of different information services.

Furthermore, in the service definition table (FIG. 7), the priority corresponding to the combination of the sensors 160 is set in the same information service.

The priority is indicated, for example, by a numerical value 0, 1, 2, 3, . . . and a combination of the sensors 160 assigned a small numerical value is used with high priority.

When, for example, an information service is specified, the priority of the sensor 160 corresponding to this information service indicates which combination of the sensors 160 should be used with high priority depending on whether all of the sensors 160 necessary to improve the accuracy, response speed and details or the like of the information service can be used or only some of the sensors 160 can be used.

Here, in an information service to provide health information, if a case where an optimal result is obtained when the brain wave sensors 168 (high accuracy, 3 sensors), blood pressure sensor 166 (high accuracy, 1 sensor), pulsation sensor 164 (high accuracy, 1 sensor) and body temperature sensor 172 (high accuracy, 1 sensor) are used is assumed to be a specific example, the combination of sensors 160 is set in a service definition table accompanied by priority.

However, depending on the configuration (environment) of the portable terminal 2, there can be a case where the sensor 160 included in the combination in which the optimal result is obtained is not available.

In such a case, the brain wave sensor 168 (high accuracy, 1 sensor), pulsation sensor 164 (medium accuracy, 1 sensor) and body temperature sensor 172 (low accuracy, 1 sensor) are set in the service definition table accompanied by priority as the combination of the sensors 160 which can obtain the next best result.

Thus, by setting a combination of a plurality of sensors 160 for the same information service, even if the combination of sensors 160 which can obtain the best result cannot be used in a certain mobile station 2, combining the sensors 160 that can obtain the next best result makes it possible to realize an information service desired by the user of the mobile station 2.

Next, the sensor parameter table (FIG. 8) will be explained.

Furthermore, to realize the aforementioned hybrid sensing system, a sensor parameter table is set for each sensor 160 so that the selected sensor 160 operates optimally.

In the sensor parameter table, a sensor parameter corresponding to a context to be extracted is set with a numerical value.

For example, when a video camera is used as the sensor 160, a measuring interval S (seconds) and analysis resolution p of an image or the like are set in the parameter table as sensor parameters.

In the hybrid sensing system, a combination of sensors available in the mobile station 2 is adaptively selected according to the situation with reference to the service definition table and the sensor parameter table, parameters indicating optimal operations are set in the selected sensors 160 respectively and sensor data for realizing an information service is thereby obtained.

A procedure for realizing the hybrid sensing system will be explained below.

Step 1-1: The user of the mobile station 2 specifies an information service.
Step 1-2: The service definition table is referred to and a combination of the sensors 160 with priority n (initial value of n=1) is selected in the specified information service.
Step 1-3: It is judged whether or not all sensors 160 included in the combination of the sensors 160 selected in Step 2 are available, and if only some sensors of this combination are available, the processing in Step 2 is repeated over again and a combination of sensors 160 with priority (n+1) is selected.
Step 1-4: Parameters to cause the selected sensors 160 to operate optimally are obtained for the respective sensors 160 selected through the processing in Step 3 with reference to the sensor parameter table.
Step 1-5: The sensor parameters obtained through the processing in Step 4 are set in the corresponding sensors 160.

For example, suppose a case where a combination of one blood pressure sensor 166, one pulsation sensor 164 and one body temperature sensor 172 is set as priority 1 and a combination of one pulsation sensor 164 and one body temperature sensor 172 is set as priority 2 in the service definition table of the health information service.

In this case, if only the combination of one pulsation sensor 164 and one body temperature sensor 172 is available in a certain mobile station 2, the combination of one pulsation sensor 164 and one body temperature sensor 172 with priority 2 is selected in the hybrid sensing system, and further sensor parameters corresponding to the pulsation sensor 164 and body temperature sensor 172 respectively and obtained with reference to the sensor parameter table are set in the pulsation sensor 164 and body temperature sensor 172 respectively.

Furthermore, in the hybrid sensing system, sensor data obtained from the respective sensors 160 obtained through the procedure shown below is processed and an information service specified by the user of the mobile station 2 is delivered.

Step 2-1: Sensor data considered necessary to realize the function of delivering an information service is received from the sensor 160.
Step 2-2: Processing considered necessary to realize the function for delivering the information service is performed using the sensor data received through the processing in Step 1.
Step 2-3: The information (sound, character, image, moving image or the like) obtained as a result of the information service specified by the user based on the processing in Step 2-2 is presented to the user via the display apparatus and speaker of the mobile station 2 or a large screen monitor in a commercial space or the like.

Hereinafter, the configuration of the sensor parameter table, service execution parameter table and information creation parameter table will be further explained.

As shown in FIG. 8, the sensor parameter table stores information services (Services) that can be delivered by the mobile station 2 or fixed terminal 4 and sensor parameters P (Parameters for Sensors) set in the sensor 160 (sensor drive module 286) in the respective information services and used to operate the sensors in association with each other.

The sensor parameters P are used, for example, to adjust the sensitivity or the like of the perspiration sensor 164, blood pressure sensor 166 and body temperature sensor 172 when a health check is delivered as the information service as described above.

Furthermore, when a plurality of parameters are set in one sensor 160, the sensor parameters P are used to adjust a plurality of settings corresponding to the one sensor 160.

For example, when sensitivity, a measuring time and a measuring interval or the like are set in the blood pressure sensor 166, the sensor parameters P of the blood pressure sensor 166 include a plurality of parameters used to adjust these settings.

As shown in FIG. 7, the service execution parameter table stores information services that can be delivered by the mobile station 2 or fixed terminal 4 and service execution parameters P' used for the processing in the service execution module 300 used to realize the respective information services in association with each other.

When, for example, a health check is delivered as the information service as described above, the service execution parameters P' indicate a normal body temperature and pulsation or the like of the user of the mobile station 2 or fixed terminal 4.

Furthermore, when, for example, a navigation service is delivered as the information service, the service execution parameters P' include constants for creating position information through integral processing in the direction sensor 178 and acceleration sensor 180 through the service execution module 300 and map information displayed in association with the position information, or the like.

Furthermore, the information creation parameter table stores information services (Services) that can be delivered by the mobile station 2 or fixed terminal 4 and information creation parameters P' (Parameters for Modules) used for the processing in the information creation module 310 used to realize the respective information services in association with each other as with the service execution parameter table shown in FIG. 7.

The information creation parameters P' indicate an image format when, for example, an information service is displayed on the output device 148.

The module DB 254 stores the service execution module 300 and information creation module 310 (FIG. 5) used for an information service that can be delivered by the mobile station 2 or fixed terminal 4 so as to be accessible from the module selection section 252 and information acquisition section 262.

The module selection section 252 selects and reads the service execution module 300 and information creation module 310 used for information services judged realizable by the module execution control section 266 out of the specified information services according to the information reported from the input analysis section 240 and loads the service execution module 300 and information creation module 310 into the module execution control section 266.

The sensor drive module DB 274 stores the sensor drive module 286 that matches the sensor 160 used for an information service that can be delivered by the mobile station 2 or fixed terminal 4 so as to be accessible from the sensor selection section 272.

The sensor selection section 272 selects and reads the sensor drive module 286 used for an information service judged realizable by the module execution control section 266 out of the specified information services according to the information reported from the input analysis section 240 and outputs the sensor drive module 286 to the sensor control section 270.

Furthermore, the sensor selection section 272 judges whether or not a combination of the sensors 160 considered necessary to obtain sensor data capable of improving the accuracy, response speed and details or the like of the specified information service is available and reports the combination of the sensors 160 judged available to the parameter setting section 246.

For example, when one blood pressure sensor 166, one pulsation sensor 164 and two brain wave sensors 168 are available in a health check service, the sensor selection section 272 can obtain the best result, whereas when all these sensors are not available but only one blood pressure sensor 166 and pulsation sensor 164 are available, the sensor selection section 272 judges that the combination of these two sensors is available and reports this judgment to the parameter setting section 246.

The sensor control section 270 sets and executes the sensor parameters P set by the parameter setting section 246 in the sensor drive module 286 inputted from the sensor selection section 272 and operates the sensor 160.

The sensor 160 is operated by the sensor drive module 286 to detect information corresponding to the respective types and return the detection result to the sensor drive module 286.

The sensor control section 270 outputs the detection result inputted from the sensor 160 to the sensor output processing section 278 as the sensor information.

The sensor output processing section 278 loads the sensor information inputted from the sensor drive module 286 into the module execution control section 266.

Furthermore, the module execution control section 266 processes the report from the input analysis section 240, judges, when other information services are already being executed, whether or not resources considered necessary to realize a newly specified information service and information services already being executed overlap between these services and estimates the amount of processing considered necessary for each information service.

The module execution control section 266 judges which information service is realizable from the overlap of resources between the newly specified information service and information service already being realized, processing capacity considered necessary to realize each information service and the remaining processing capacity of the mobile station 2 or fixed terminal 4 obtained from the OS operating on the mobile station 2 or fixed terminal 4 and reports the information service judged realizable to the parameter setting section 246, module selection section 252 and sensor selection section 272.

In order to realize a realizable information service out of the specified services, the module execution control section 266 sets the sensor 160 (sensor drive module 286), the service execution module 300 and information creation module 310 loaded from the module selection section 252 so as to perform input/output according to information indicating the input/output relationships inputted from the input analysis section 240.

Furthermore, the module execution control section 266 sets the service execution parameters P' and information creation parameters P' inputted from the parameter setting section 246 in the loaded service execution module 300 and information creation module 310.

The module execution control section 266 executes the service execution module 300 and information creation module 310 on which these settings are performed and realizes one or more information services.

Furthermore, the module execution control section 266 outputs the information service result of the realized information service to the information generation section 258.

The information generation section 258 creates information to be outputted to the user from the result of the information service inputted from the module execution control section 266 and outputs the information to the information output section 232 of the service delivery section 22.

[Server Program 60]

Hereinafter, a server program 60 executed by the module/parameter server apparatus 6 shown in FIG. 1 will be explained.

Figure 9:
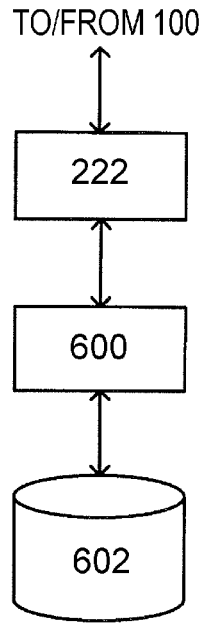
FIG. 9 illustrates a server program executed in the server apparatus shown in FIG. 1.

FIG. 9 illustrates the server program 60 executed by the module/parameter server apparatus 6 shown in FIG. 1.

As shown in FIG. 9, the server program 60 is made up of a communication processing section 222, a DB searching section 600 and a module/parameter DB 602.

The server program 60 receives a request from the mobile station 2 or fixed terminal 4 using these components and returns a requested module or parameter.

In the server program 60, the module/parameter DB 602 stores modules and parameters considered necessary for an information service delivered to the mobile station 2 or fixed terminal 4 so as to be referred to from the DB searching section 600.

The DB searching section 600 reads one or more modules and parameters requested from the mobile station 2 or fixed terminal 4 from the module/parameter DB 602 and transmits the modules and parameters to the mobile station 2 or fixed terminal 4 via the communication processing section 222 and network 100.

[Web Program 80]

Hereinafter, a Web program 80 executed by the Web server 8 shown in FIG. 1 will be explained.

Figure 10:
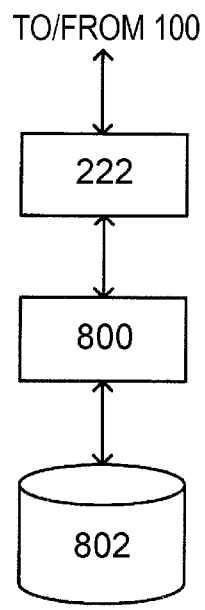
FIG. 10 illustrates a Web program executed by the Web server shown in FIG. 1.

FIG. 10 illustrates the Web program 80 executed by the Web server 8 shown in FIG. 1.

As shown in FIG. 10, the Web program 80 is made up of a communication processing section 222, a Web data delivering section 800 and a Web content DB 802.

Upon receiving a request from the mobile station 2 or fixed terminal 4, the Web program 80 returns a requested Web content using these components.

In the Web program 80, the Web content DB 802 stores Web contents delivered to or displayed in the mobile station 2 or fixed terminal 4 so as to be accessible from the Web data delivering section 800.

The Web data delivering section 800 reads a Web content from the Web data delivering section 800 at the request from the mobile station 2 or fixed terminal 4 and transmits the Web content to the mobile station 2 or fixed terminal 4 that sent the request via the service delivery section 22 and network 100.

[Operation of Information Service Delivery System 1 According to First Embodiment]

Hereinafter, operations of the information service delivery system 1 according to the first embodiment will be explained.

Figure 11A:
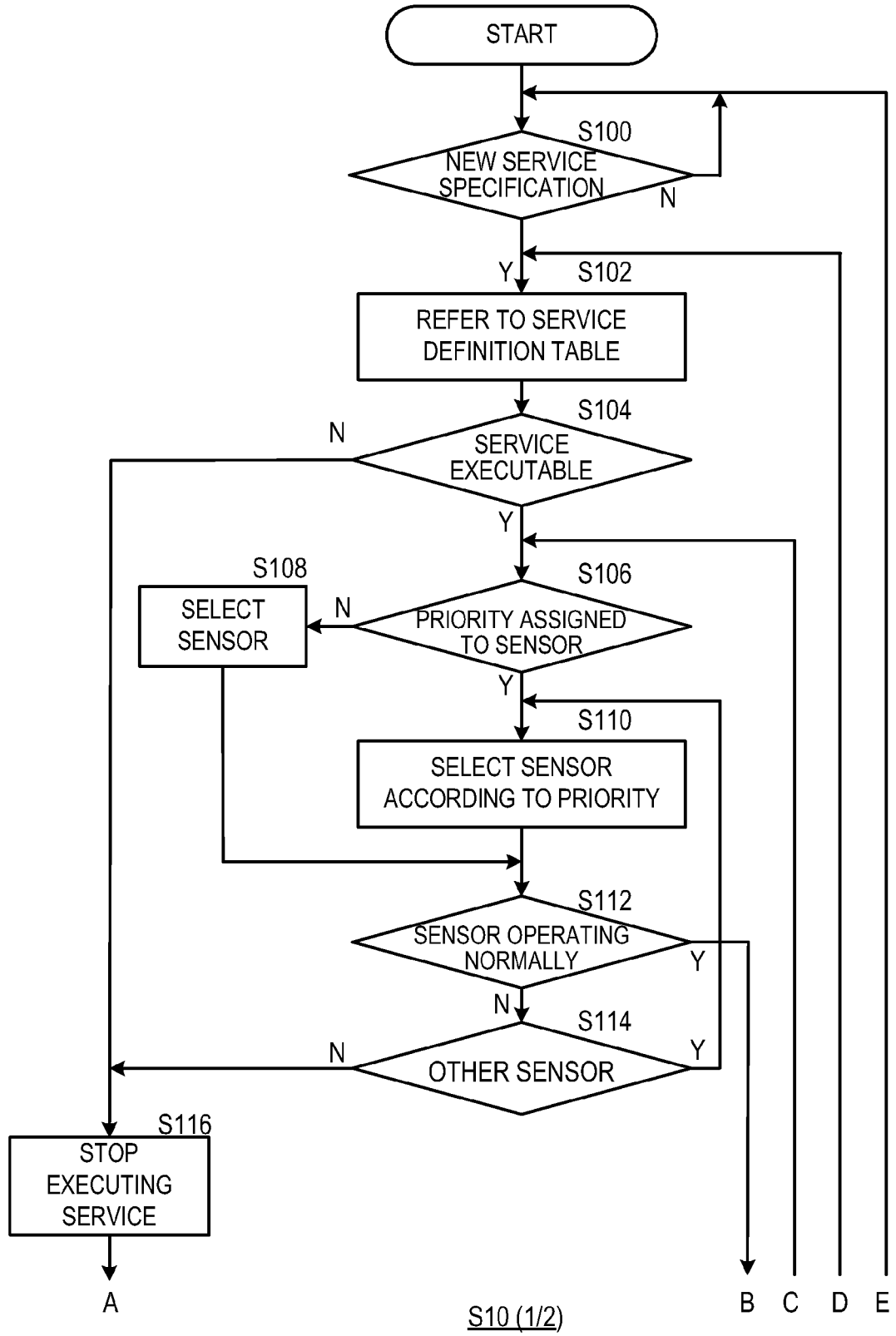
FIG. 11A is a first flowchart illustrating operations of the information service delivery system shown in FIG. 1 according to a first embodiment.
Figure 11B:
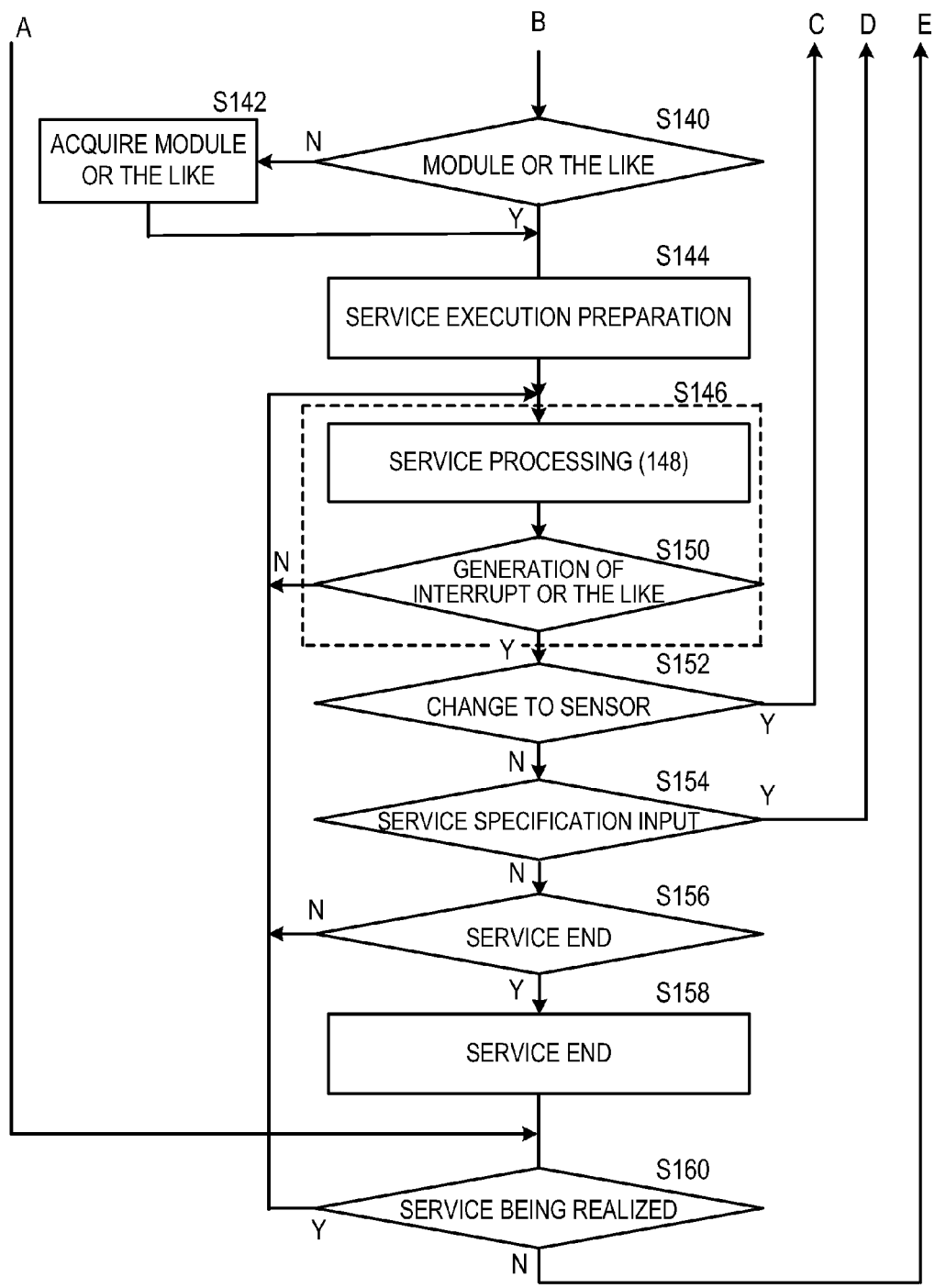
FIG. 11B is a second flowchart illustrating operations of the information service delivery system shown in FIG. 1 according to the first embodiment.

FIG. 11A and FIG. 11B are first and second flowcharts illustrating an operation S10 according to the first embodiment of the information service delivery system 1 shown in FIG. 1.

A to E shown in FIG. 11A and FIG. 11B indicate that lines assigned the same reference numerals are connected together across these figures and represent processing flows.

As shown in FIG. 11A and FIG. 11B, in step 100 (S100), when the mobile station 2 or fixed terminal 4 starts the terminal program 20 (FIG. 4) and the module/parameter server apparatus 6 starts the server program 60 (FIG. 9), the application input section 230 of the terminal program 20 judges whether or not the user of the mobile station 2 or fixed terminal 4 has performed an operation of specifying a new information service on the input device 146 (UI 220).

When the operation has been performed, the terminal program 20 moves to processing in S102 or remains at the processing in S100 otherwise.

In step 102(S102), the input analysis section 240 receives specification of an information service via the application input section 230, refers to the service definition table (FIG. 6) stored in the input analysis DB 242, finds which module and parameter are necessary to realize the specified service and reports the module and parameter to the module execution control section 266 or the like.

Furthermore, the module execution control section 266 processes the report from the input analysis section 240 and judges, when another information service is already being executed, whether or not resources considered necessary to realize a newly specified information service and information services already being executed overlap between these services.

Furthermore, the module execution control section 266 estimates the amount of processing considered necessary for the newly specified information service.

Furthermore, the sensor selection section 272 judges whether or not a combination of sensors 160 considered necessary to obtain sensor data capable of improving the accuracy, response speed and details or the like of the specified information service is available.

In step 104 (S104), the module execution control section 266 judges whether or not each information service can be executed based on the overlap of resources judged above, the remaining processing capacity of the mobile station 2 or fixed terminal 4 obtained from the OS being executed on the mobile station 2 or fixed terminal 4, the amount of processing estimated above and priority of each information service defined in the service definition table.

The terminal program 20 moves to processing in S116 when there is an information service that is not executable, the module execution control section 266 and sensor control section 270 perform processing for stopping the execution of the information service that is not executable (S116), or the terminal program 20 moves to processing in S106 otherwise.

In step 106 (S106), the sensor selection section 272 judges whether or not priority is assigned to the sensor 160 considered necessary to realize the newly specified information service in the service definition table (FIG. 6).

The terminal program 20 moves to processing in S110 when priority is assigned to the sensor 160 or moves to processing in S108 otherwise.

In step 108 (S108), the sensor selection section 272 selects a sensor 160 (sensor drive module 286) considered necessary to realize the newly specified information service in the service definition table (FIG. 6).

Furthermore, the sensor selection section 272 judges whether or not the combination of sensors 160 necessary to obtain sensor data capable of optimizing the accuracy, response speed and details or the like of the specified information service is available.

When the combination of sensors 160 is not available, the sensor selection section 272 judges whether or not a combination of sensors having the next priority is available in the same information service.

In step 110 (S110), the sensor selection section 272 selects a sensor 160 never considered as a target of the processing in S110 at that time yet and assigned the highest priority in the service definition table out of the available sensors 160 considered necessary to realize the newly specified information service.

In step S112 (S112), the sensor control section 270 judges whether or not the sensor 160 selected in the processing in S110 is operating normally.

When the sensor 160 is operating normally (e.g., when the GPS 176 is normally receiving a radio wave signal in a navigation service), the sensor control section 270 moves to processing in S140 or moves to processing in S114 otherwise.

In step 114 (S114), the sensor selection section 272 judges whether or not there are any other sensors 160 that are not processing targets in S110 at that time out of the sensors 160 considered necessary to realize the newly specified information service.

The terminal program 20 returns to the processing in S110 where there are other sensors 160 or moves to processing in S116 otherwise and the module execution control section 266 and the sensor control section 270 perform processing for stopping the newly specified information service.

In step 140 (S140), the information acquisition section 262 judges whether or not all modules and parameters (FIG. 5 to FIG. 7) necessary to realize the newly specified information service exist in the terminal program 20.

When all the necessary modules and parameters exist in the terminal program 20, the terminal program 20 moves to processing in S142 or moves to processing in S144 otherwise.

In step 142 (S142), the module execution control section 266 sets the parameter inputted from the parameter DB 248 in the module loaded from the module selection section 252, performs a setting so that information is delivered so as to be suitable for the realization of the newly specified information service between the module, middleware 24 and sensor drive section 28 and prepares for the execution of the information service.

In step 146 (S146), the module execution control section 266 performs processing for realizing each information service and outputs the result of each information service via the information generation section 258 and UI 220 as appropriate (S148).

While performing processing for realizing each information service, the module execution control section 266 specifies a new information service and judges whether or not an interrupt signal and a report from the OS have been generated indicating that the sensor 160 (sensor drive module 286) which has been operating normally stops operating normally or the sensor 160 which has not been operating normally starts operating normally (S150).

The module execution control section 266 moves to processing in S152 when an interrupt is generated or remains at the processing in S146 otherwise.

In step 152 (S152), the module execution control section 266 judges whether or not a changes has occurred in the state of the sensor 160 (sensor drive module 286) operating to realize each information service.

That is, the module execution control section 266 judges whether or not an event accompanying a variation in the state of the sensor has occurred in which the sensor 160 (sensor drive module 286) which has been operating normally stops operating normally or the sensor 160 which has not been operating normally starts operating normally.

When an event accompanying a variation in the state of a sensor used to realize a certain information service occurs, the terminal program 20 assumes that the sensor 160 used to realize this information service is not any target of the processing in S110 and returns to the processing in S106 or moves to processing in S154 otherwise.

In step 154 (S154), the module execution control section 266 judges whether or not the generation of the interrupt or the like detected in S148 indicates specification of a new service.

When the generation of the interrupt indicates specification of a new service, the terminal program 20 moves to processing in S102 or moves to processing in S156 otherwise.

In step 156 (S156), the module execution control section 266 judges whether or not the generation of the interrupt detected in S148 indicates an end of a certain information service being realized.

When the generation of the interrupt or the like indicates an end of the information service being realized, the terminal program 20 moves to processing in S158 or performs processing accompanying the interrupt or the like as appropriate otherwise and returns to processing in S146.

In step 158 (S158), the module execution control section 266 performs processing for ending the information service judged to be ended in the processing in S156.

In step 160 (S160), the module execution control section 266 judges whether or not there is any information service being realized other than the information service ended in the processing in S158.

When there is an information service being realized, the terminal program 20 returns to the processing in S146 or returns to the processing in S100 otherwise.

[Example of Information Service]

Hereinafter, the first and second information services delivered by the mobile station 2 or fixed terminal 4 will be illustrated.

FIG. 6 and FIG. 7 illustrate the service definition table, sensor parameter table, service execution parameter table and information creation parameter table to realize the following three examples.

Furthermore, each information service shown below is only an illustration and the information service delivered by the mobile station 2 or fixed terminal 4 is not limited to these three types.

[Health Check]

Hereinafter, operations of the mobile station 2 or fixed terminal 4 will be explained using the delivery of a first health check whereby the health condition of the user is checked by the mobile station 2 or fixed terminal 4 as a specific example.

FIG. 12 illustrates a first information service (health check) delivered by the mobile station 2 or fixed terminal 4.

As shown in FIG. 12, when the mobile station 2 or fixed terminal 4 realizes a health check as an information service, for example, the pulsation sensor 162, blood pressure sensor 166 and body temperature sensor 172 are selected as the sensors 160, and the sensor drive modules 286-1,286-2 and 286-5 that match these sensors are loaded in the sensor control section 270 and executed.

Furthermore, for example, the sensor information indicating body information such as pulse rate, blood pressure and body temperature of the user is periodically collected from the sensor 160 as sensor information, the service execution module 300-1 that generates numerical values that comprehensively show such information is loaded into the module execution control section 266.

Furthermore, the numerical values generated by the service execution module 300-1 are compared with determination data 302 set as a service execution parameter, and the service execution module 300-2 that comprehensively determines the health of the user of the mobile station 2 or fixed terminal 4 is loaded into the module execution control section 266.

Furthermore, the information creation module 310-1 that creates the result of the health check in a predetermined image format from the determination result of the service execution module 300-2 is loaded into the module execution control section 266.

The module execution control section 266 inputs the sensor information from the sensor drive modules 286-1, 286-2 and 286-5 to the service execution module 300-1 so that the sensor information is processed and causes the processing result to be outputted to the information creation module 310-2.

The service execution module 300-2 determines the processing result inputted from the service execution module 300-1 and outputs the determination result to the information creation module 310.

The information creation module 310-1 creates a result of the health check from the determination result inputted from the service execution module 300-1 in a predetermined format, outputs the health check result to the information output section 232 (FIG. 4) via the information generation section 258 and presents the health check result to the user.

The information creation module 310-1 may display the body information obtained from the sensors 160 together with the determination result on the output device 148.

Furthermore, a plurality of types may be provided in the health check.

For example, for a health check focused on the movement of the user's heart, the service definition table (FIG. 6) may be set so that the pulsation sensor 162, blood pressure sensor 166, perspiration sensor 162, heart signal sensor 170, body temperature sensor 172, blood component sensor 174 and temperature/humidity sensor 184 are used as the sensors 160 and appropriate parameters may be set in the sensor parameter table, service execution parameter table and information creation parameter table for this purpose.

In this case, as priority corresponding to the respective sensors 160 used, maximum priority 1 is assigned to the heart signal sensor 170; next priority 2 to the pulsation sensor 162 and blood pressure sensor 166; and minimum priority 3 to the other sensors 160 in the service execution parameter table.

Furthermore, for a health check focused on the amount of exercise of the user, a setting is likewise made in the service execution parameter table so that the pulsation sensor 162, perspiration sensor 164, heart signal sensor 170, body temperature sensor 172 and pedometer 188, body temperature sensor 172, acceleration sensor 180 and speed sensor 182 are used.

In this case, maximum priority 1 is assigned to the pulsation sensor 162, pedometer 188, heart signal sensor 170 and body temperature sensor 172 and next priority 2 is assigned to the other sensors 160 out of the sensors 160 used.

Furthermore, for example, for a health check focused on the state of the user's brain, a setting is made in the service execution parameter table so that the blood pressure sensor 166, brain wave sensor 168, heart signal sensor 170, body temperature sensor 172 and blood component sensor 174 are used.

In this case, for example, maximum priority 1 is assigned to the brain wave sensor 168; next priority 2 to the heart signal sensor 170 and blood component sensor 174; and minimum priority 3 to the other sensors 160 out of the sensors 160 used.

Furthermore, for example, in a certain health check service, the best result may be obtained when one blood pressure sensor 166, one pulsation sensor 164 and two brain wave sensors 169 (first combination) are used, the next best result may be obtained when one blood pressure sensor 166 and pulsation sensor 164 (second combination) are used and the third best result may be obtained when only one blood pressure sensor 166 (third combination) is used.

In such a case, priority is set for a combination of the sensors 160 such that maximum priority 1 is assigned to the first combination; next priority 2 to the second combination; and minimum priority 3 to the third combination.

[Navigation Service]

Hereinafter, operations of the mobile station 2 or fixed terminal 4 will be explained using a navigation service whereby the location of the mobile station 2 or fixed terminal 4 is displayed on a map as a specific example.

Figure 13:
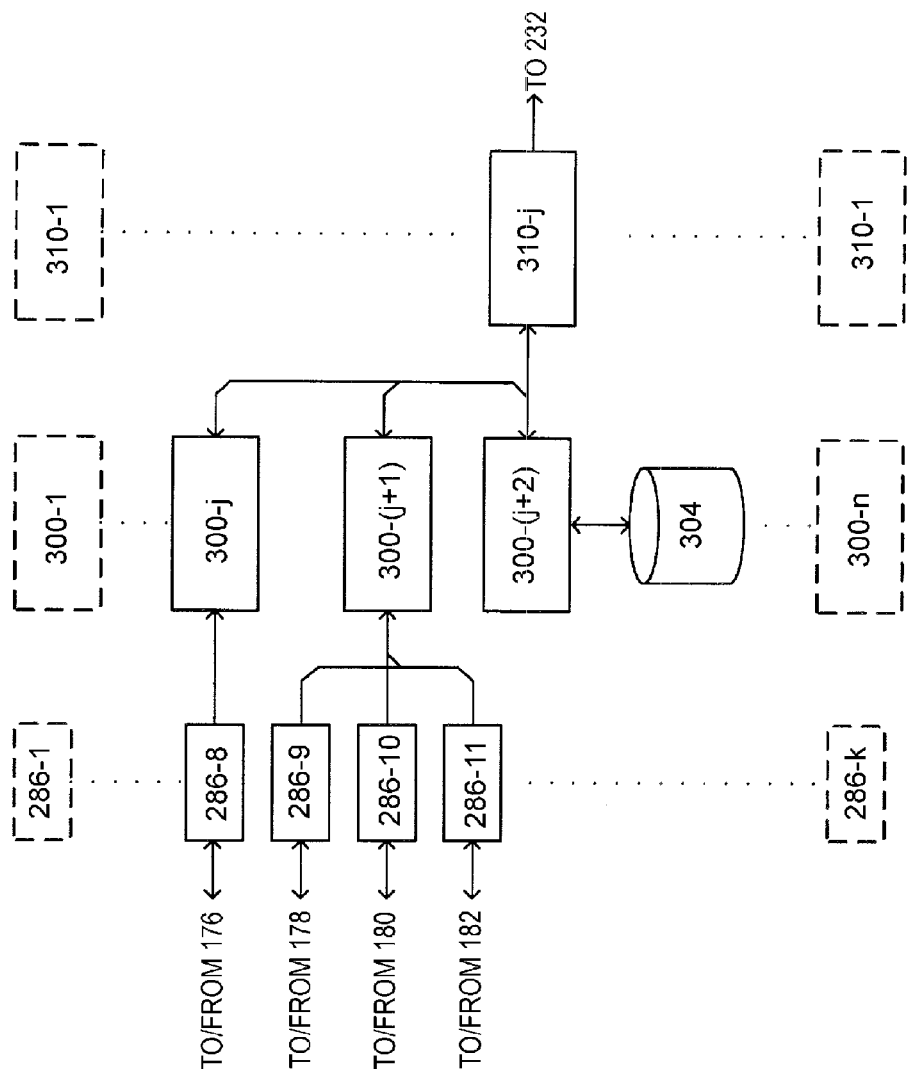
FIG. 13 illustrates a second information service (navigation service) delivered by the mobile stations and fixed terminals shown in FIG. 1.

FIG. 13 illustrates a second information service (navigation service) delivered by the mobile station 2 or fixed terminal 4.

As shown in FIG. 13, when the mobile station 2 or fixed terminal 4 delivers a navigation service as the information service, for example, the GPS 176, direction sensor 178, acceleration sensor 180 and speed sensor 182 are selected as the sensors 160 and the sensor drive modules 286-8, 286-9, 286-10 and 286-11 that match these sensors are loaded into the sensor control section 270 and executed.

Furthermore, for example, a service execution module 300-*j* that calculates the latitude/longitude of the mobile station 2 or fixed terminal 4 from the sensor information inputted from the GPS 176 is loaded into the module execution control section 266.

Furthermore, a service execution module 300-(*j*+1) that performs integral processing on the sensor information inputted from the direction sensor 178, acceleration sensor 180 and speed sensor 182 and calculates the latitude/longitude of the mobile station 2 or fixed terminal 4 is loaded into the module execution control section 266.

Furthermore, a service execution module 300-(*j*+2) that sets map data 304 as a service execution parameter, creates map data corresponding to the latitude/longitude from the service execution module 300-*j* when the GPS 176 is normally operating and creates map data corresponding to the latitude/longitude from the service execution module 300-(*j*+1) when the GPS 176 is not normally operating is loaded into the module execution control section 266.

Furthermore, an information creation module 310-*j* that creates a result of a navigation service from the map data created by the service execution module 300-(*j*+2) in a predetermined format is loaded into the module execution control section 266.

When the GPS 176 whose priority is higher than that of the direction sensor 178, acceleration sensor 180 and speed sensor 182 is operating normally, the module execution control section 266 causes the service execution module 300-*j* to process the sensor information from the sensor drive module 286-8, and causes the processing result thereof to be outputted to the information creation module 310-*j*.

When the GPS 176 is not operating normally, the module execution control section 266 causes the service execution module 300-(*j*+1) to process the sensor information from the sensor drive modules 286-9, 286-10 and 286-11 corresponding to the direction sensor 178, acceleration sensor 180 and speed sensor 182 and to output the processing result thereof to the service execution module 300-(*j*+2).

When the GPS 176 returns from a state of not operating normally to a state of operating normally, the module execution control section 266 causes the service execution module 300-*j* to process the sensor information from the sensor drive module 286-8 and to output the processing result thereof to the service execution module 300-(*j*+2).

The service execution module 300-(*j*+2) creates map data corresponding to the processing result (latitude/longitude) inputted from the service execution module 300-*j* or service execution module 300-(*j*+1) and outputs the map data to the information creation module 310-*j* as the processing result.

The information creation module 310-*j* creates a result of a navigation service from the map data inputted from the service execution module 300-(*j*+2) in a predetermined format, outputs the navigation service result to the information output section 232 (FIG. 4) via the information generation section 258 and presents the navigation service result to the user.

The navigation service using the GPS 176 and the navigation service using the direction sensor 178, acceleration sensor 180 and speed sensor 182 may be defined in the service definition table or the like as independent information services and any one of the services may be realized according to the specification by the user.

[Image Information Creation Service]

Hereinafter, operations of the mobile station 2 or fixed terminal 4 will be explained using a delivery of an image information creation service whereby image data taken by the camera 150 (FIG. 2) or the like is stored with the location of image taking and a comment or the like added thereto as a specific example of the information service.

Figure 14:
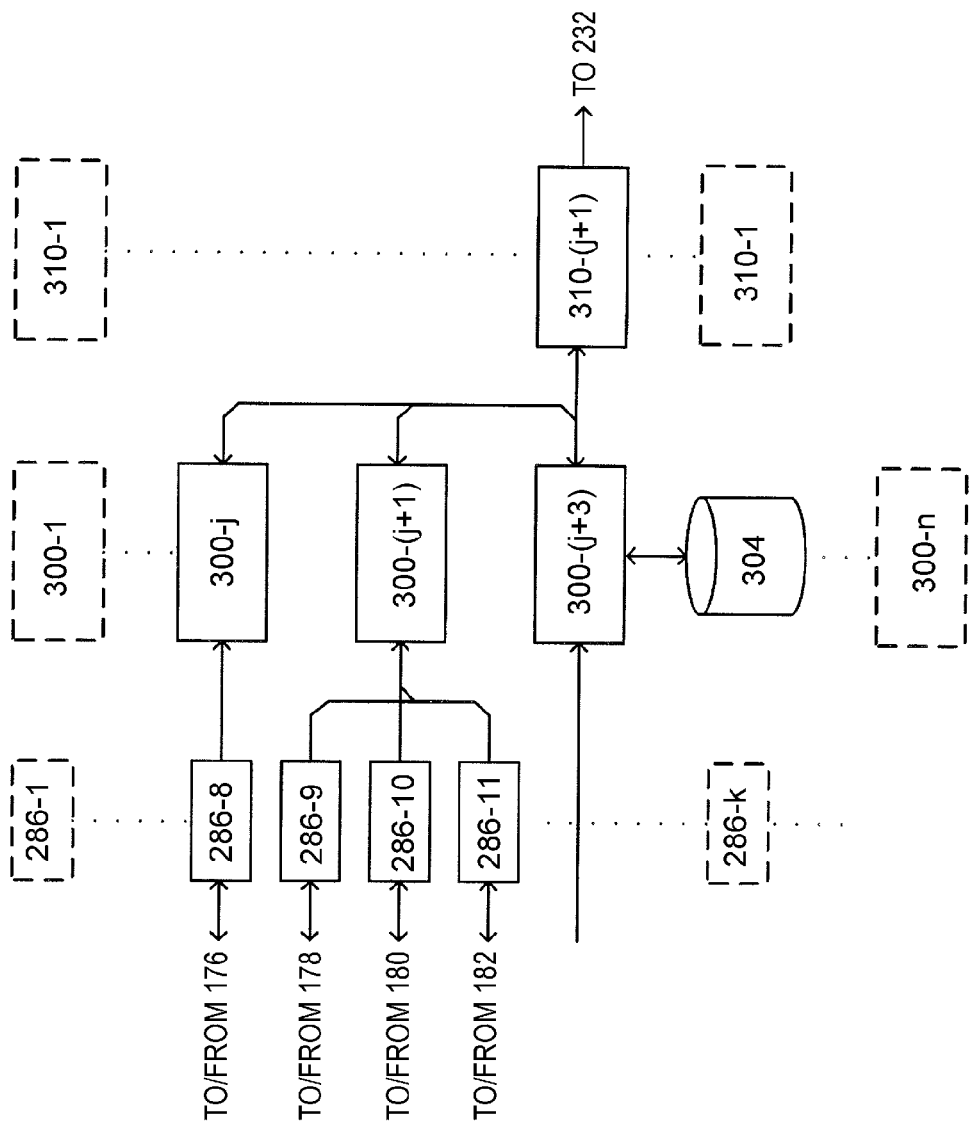
FIG. 14 illustrates a third information service (image information creation service) delivered by the mobile stations and fixed terminals shown in FIG. 1.

FIG. 14 illustrates a third information service (image information creation service (Image Data) delivered by the mobile station 2 or fixed terminal 4 shown in FIG. 1.

To deliver an image information creation service, the service execution module 300-(*i*+3) and information creation module 310-(*i*+1) are used instead of the service execution module 300-(*i*+2) and information creation module 310-*i* used in the navigation service.

In addition to the function of the service execution module 300-(*i*+2), the service execution module 300-(*i*+3) adds additional information such as the position information (latitude/longitude) of the mobile station 2 or fixed terminal 4 obtained by any one of the service execution modules 300-*i* and 300-(*i*+1) and, map information indicating the image taking locations and comment text or the like inputted from the input device 146 to the moving image and still image taken by the camera 150 and outputs the images to the information creation module 310-(*i*+1) as the processing result.

This additional information can be added to the images in an arbitrary mode or at arbitrary timing specified by the user via the input device 146.

For example, the additional information may be added to a still image, added to a series of (corresponding to one scene) moving images respectively, may be visibly added to an image or may be invisibly added to an image.

The information creation module 310-($i$+1) creates a result of a predetermined information service from the processing result inputted from the service execution module 300-($i$+3), outputs the result to the output device 148 via the information output section 232 or stores the result in the memory 142 or a memory card (not shown) or the like inserted in the CPU peripheral apparatus 144.

The service definition table shown in FIG. 6 defines sensors, service execution module 300 and information creation module 310 used in a plurality of types of health checks, a plurality of types of navigation services and a plurality of types of image information creation services respectively.

Furthermore, appropriate parameters are set in the sensor parameter table, service execution parameter table and information creation parameter table shown in FIG. 8 and FIG. 7 for the respective services.

Furthermore, when it is not necessary to acquire modules and parameters from the module/parameter server apparatus 6, the mobile station 2 used in the third information service shown here can be realized by, for example, a single digital camera provided with sensors such as a GPS function and the pulsation sensor 162.

By preparing the aforementioned plurality of types of health checks, definitions of various types of navigation services and various types of image information creation services, setting of parameters and the sensor drive module 286, service execution module 300 and information creation module 310 matching these information services, it is possible to deliver various types of health checks, various types of navigation services and various types of image information creation services according to specification of the user of the mobile station 2 or fixed terminal 4.

Likewise, in addition to the three types of information service described so far, by preparing definitions of information services, setting of parameters and the sensor drive module 286, service execution module 300 and information creation module 310 necessary to deliver information services as appropriate, it is possible to deliver various types of information services other than these services.

Second Embodiment

Hereinafter, a second embodiment disclosed in the present application will be explained using as a specific example, a Web browsing service devised so as to be able to detect components of a Web content of interest to a user who browses the Web content by changing the operation of the terminal program 20 (FIG. 4) as an information service in the information service delivery system 1.

FIG. 15 is a second diagram illustrating a service definition table stored in the input analysis DB 242 shown in FIG. 4.

The input analysis DB 242 stores the second service definition table shown in FIG. 15 so as to be referred to by the input analysis section 240.

Hereinafter, differences between the first service definition table shown in FIG. 6 and the second service definition table shown in FIG. 15 will be further explained.

In the second service definition table, information services that can be delivered by the mobile station 2 or fixed terminal 4 (FIG. 1) are associated with one or more combinations of sensors 160 used for the respective information services (Services; S#1 to S#n) that can be delivered.

Priority of a combination of sensors 160 used is indicated by a numerical value such as 1, 2, 3, . . . , and FIG. 15 illustrates a case where high priority 1 is set in a first combination of the sensors 160 used to realize the above described Web browser (Web Browser) function S#m (pulsation sensor 162, perspiration sensor 164, brain wave sensor 168 and viewpoint detection sensor 186) and low priority 2 is set in a second combination (pulsation sensor 162 and perspiration sensor 164) as the information services.

FIG. 16 is a second diagram illustrating the sensor parameter table stored in the parameter DB 248 shown in FIG. 4.

FIG. 17 is a second diagram illustrating the service execution parameter table stored in the parameter DB 248 shown in FIG. 4.

The parameter DB 248 stores the sensor parameter table shown in FIG. 16, the service execution parameter table shown in FIG. 17 and an information creation parameter table having a configuration similar to that of the service execution parameter table shown in FIG. 17 so as to be referred to from the parameter setting section 246 and information acquisition section 262.

As shown in FIG. 16, the sensor drive modules 286-1, 286-2, 286-4 and 286-13 corresponding to the pulsation sensor 162, perspiration sensor 164, brain wave sensor 168 and viewpoint detection sensor 186, and sensor parameters $P_{mp}$ and $P_{m(p+1)}$ set in the service execution modules 300-$p$ to 300-($p$+2) are set in the sensor parameter table used to realize the above described Web browser function.

Furthermore, as shown in FIG. 17, the service execution parameters and information creation parameters are set in the service execution parameter table and information creation parameter table respectively in correspondence with the service execution module 300 and information creation module 310 used to realize the above described Web browser function.

[Operation of Information Service Delivery System 1 According to Second Embodiment]

Hereinafter, operations of the information service delivery system 1 according to the second embodiment will be explained.

Figure 18A:
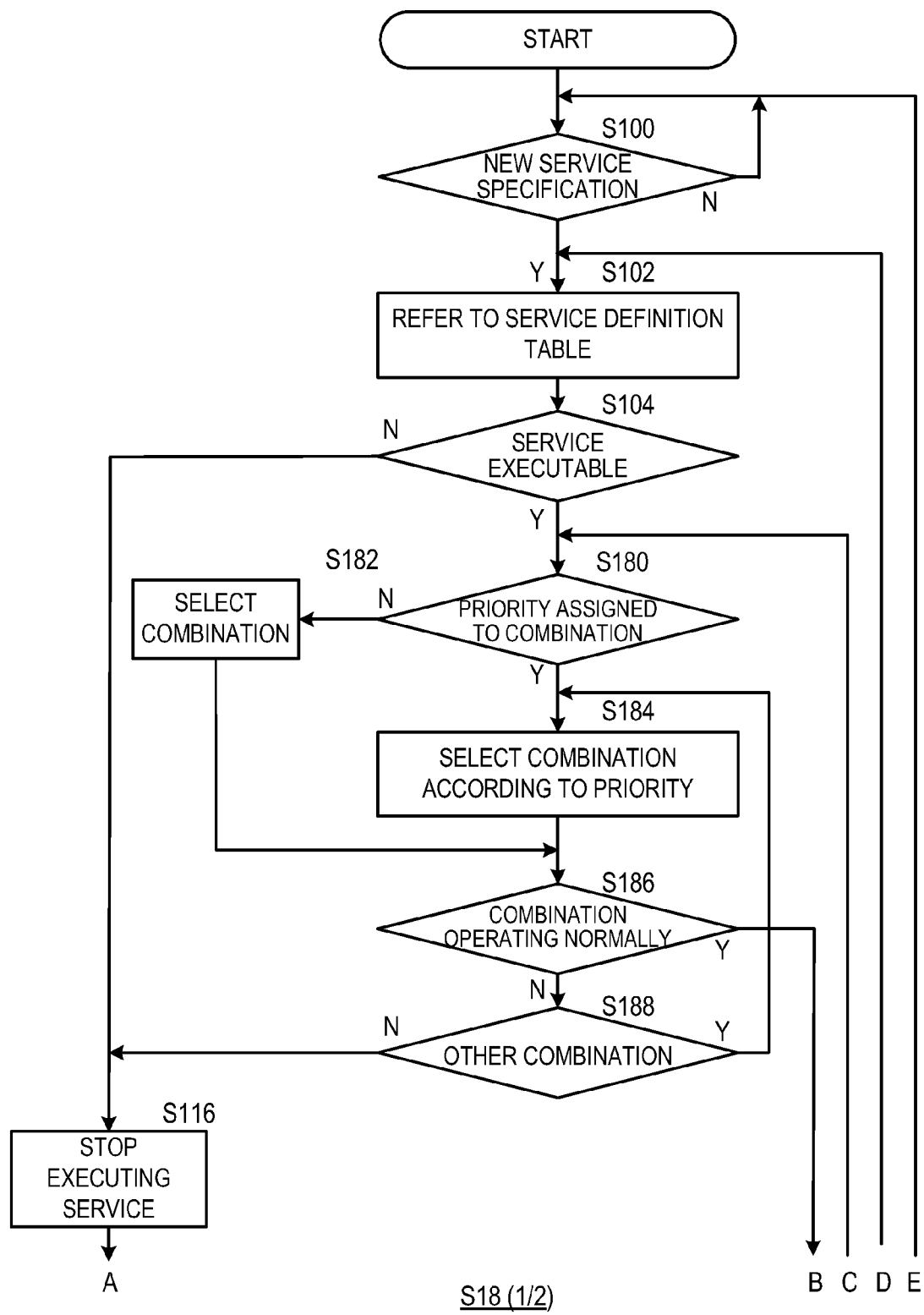
FIG. 18A is a first flowchart illustrating operations (S18) of the information service delivery system shown in FIG. 1 according to a second embodiment.
Figure 18B:
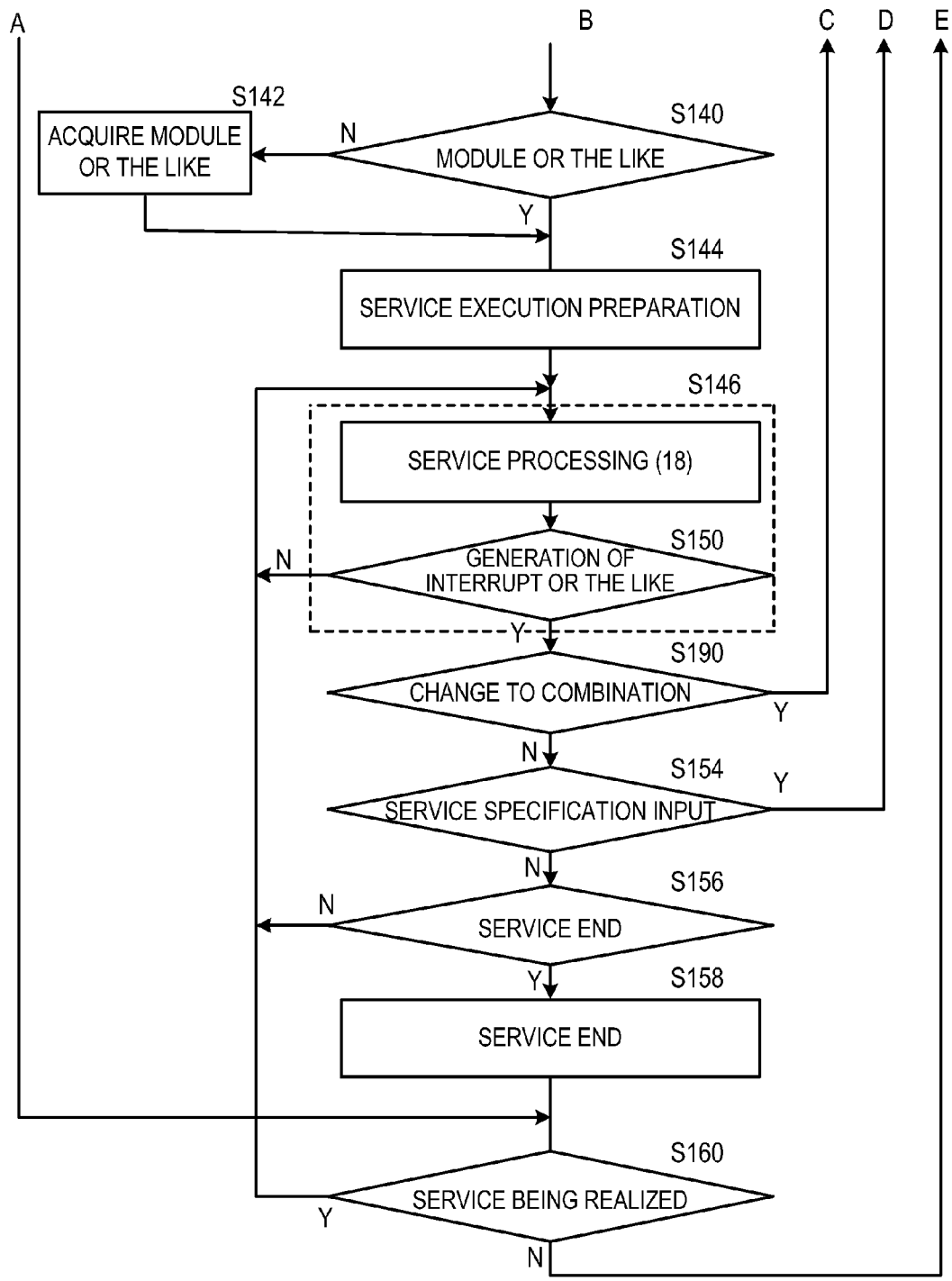
FIG. 18B is a second flowchart illustrating operations (S18) of the information service delivery system shown in FIG. 1 according to the second embodiment.

FIG. 18A and FIG. 18B are first and second flowcharts illustrating operations (S18) of the information service delivery system shown in FIG. 1 according to the second embodiment.

[Operation of Information Service Delivery System 1 According to First Embodiment]

Hereinafter, operations of the information service delivery system 1 according to the first embodiment will be explained.

FIG. 11A and FIG. 11B are the first and second flowcharts illustrating operations S10 of the information service delivery system 1 shown in FIG. 1 according to the first embodiment.

A to E shown in FIG. 11A and FIG. 11B indicate that lines assigned the same reference numerals are connected together across these figures and represent processing flows.

As shown in FIG. 11A and FIG. 11B, when the mobile station 2 or fixed terminal 4 starts the terminal program 20 (FIG. 4) and the module/parameter server apparatus 6 starts the server program 60 (FIG. 9), and when the Web server 8 starts the Web program 80 (FIG. 10), the terminal program 20 performs processing in S100 shown in FIG. 11A.

In step 102 (S102), the terminal program 20 performs processing similar to the processing in S102 shown in FIG. 11A.

That is, the input analysis section 240 of the terminal program 20 performs processing with reference to the service definition table (FIG. 16) and the module execution control section 266 performs processing for estimating the amounts of overlapping and processing of resources.

In step 104 (S104), the terminal program 20 performs processing similar to the processing in S104 shown in FIG. 11A and performs processing, when there is any non-executable information service, for stopping such an information service (S116) or moves to processing in S180 otherwise.

In step 180 (S180), the sensor selection section 272 judges whether or not priority is assigned to the combination of the sensors 160 considered necessary to realize a newly specified information service in the service definition table (FIG. 16).

The terminal program 20 moves to processing in S184 when priority is assigned to the combination of the sensors 160 or moves to processing in S182 otherwise.

In step 182 (S182), the sensor selection section 272 selects a combination of the sensors 160 (sensor drive module 286) considered necessary to realize the newly specified information service in the service definition table (FIG. 15).

In step 184 (S184), the sensor selection section 272 selects a combination of the sensors 160 never considered to be the target of the processing in S180 and assigned the highest priority in the service definition table out of the combinations of the available sensors 160 considered necessary to realize the newly specified information service.

The sensor control section 270 sets sensor parameters P (FIG. 16) inputted from the parameter DB 248 in the sensors 160 selected by the sensor selection section 272 (sensor drive module 286) and starts the sensors.

In step S186 (S186), the sensor control section 270 judges whether or not all the sensors included in the combination of the sensors 160 (sensor drive module 286) started in the processing in S184 are operating normally.

When the sensors 160 are operating normally (e.g., when all the pulsation sensor 162, perspiration sensor 164, brain wave sensor 168 and viewpoint detection sensor 186 are operating normally), the sensor control section 270 moves to processing in S140 or moves to processing in S188 otherwise.

In step 188 (S188), the sensor selection section 272 judges whether or not there is any combination of the other sensors 160 not considered to be the targets of the processing in S180 at that time out of the combinations of the sensors 160 (sensor drive module 286) considered necessary to realize the newly specified information service.

The terminal program 20 returns to the processing in S180 when there is any combination of the other sensors 160 or moves to processing in S116 otherwise, and the module execution control section 266 and sensor control section 270 perform processing for stopping the newly specified information service.

In step 140 (S140), the terminal program 20 performs processing similar to that in S140 shown in FIG. 11B.

In step 142 (S142), the terminal program 20 performs processing similar to that in S142 shown in FIG. 11B.

In step 146 (S146), the terminal program 20 performs processing similar to that in S146 shown in FIG. 11B.

That is, the module execution control section 266 performs processing for realizing each information service and outputs a result of each information service (S148).

The terminal program 20 judges whether or not an event such as a variation in the state of the sensor has occurred while performing processing for realizing each information service (S150).

The module execution control section 266 moves to processing in S190 when an interrupt is generated or remains at processing in S146 otherwise.

In step 190 (S190), the module execution control section 266 judges whether or not a change has occurred in one or more states of the sensor 160 (sensor drive module 286) included in a combination of the sensors 160 (sensor drive module 286) operating to realize each information service.

That is, the module execution control section 266 judges whether or not an event accompanying a change in the state of the sensor has occurred in which one or more sensors 160 included in the combination of the sensors 160 which have been operating normally to realize each information service have stopped operating normally or all the sensors 160 included in the combination of the sensors 160 which have not been operating normally start operating normally.

When an event accompanying a variation in the state of the sensor used to realize a certain information service has occurred, the terminal program 20 assumes that the combination of the sensors 160 used to realize this information service is not a target of the processing in S180, returns to the processing in S180 or moves to processing in S154 otherwise.

In step 154 (S154), the terminal program 20 performs processing similar to that in S154 shown in FIG. 11B.

In step 156 (S156), the terminal program 20 performs processing similar to that in S156 shown in FIG. 11B.

In step 158 (S158), the terminal program 20 performs processing similar to that in S158 shown in FIG. 11B.

In step 160 (S160), the terminal program 20 performs processing similar to that in S160 shown in FIG. 11B.

[Display of Web Content and Detection of Matter of Interest]

Hereinafter, a fourth information service delivered by the mobile station 2 or fixed terminal 4 will be illustrated.

Figure 19:
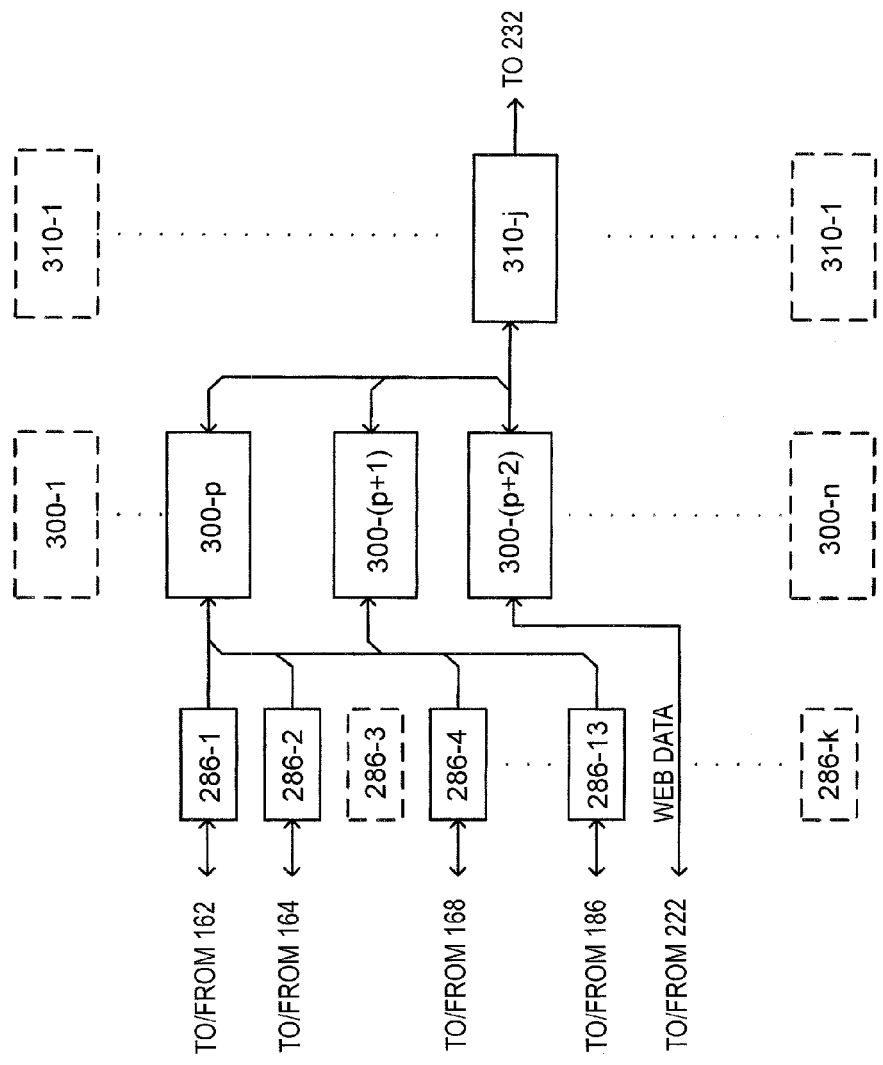
FIG. 19 illustrates an information service that detects the presence/absence of the user's interest in the display of a Web content and Web content components in the information service delivery system.

FIG. 19 illustrates an information service that displays a Web content and detects the presence/absence of the user' interest in the components of the Web content in the information service delivery system 1.

The sensor drive module 286, service execution modules 300-$p$ and 300-($p$+1) and information creation module 310-$p$ shown in FIG. 19 are selected by the module selection section 252 and their respective parameters P and P' are set by the parameter setting section 246.

In FIG. 19, the sensor drive module 286-1 causes the pulsation sensor 162 attached to the user's hand or the like to operate and detect pulsation of the user of the mobile station 2 or fixed terminal 4 and outputs information indicating the user's pulsation to the service execution module 300-$p$.

The sensor drive module 286-2 causes the perspiration sensor 164 attached to the user's hand or the like to operate and detect the presence/absence of perspiration of the user and the amount of perspiration or the like and outputs information indicating perspiration and the amount of perspiration to the service execution module 300-$p$.

The sensor drive module 286-4 causes the brain wave sensor 168 attached to the user's head or the like to operate and detect the user's brain waves and outputs information indicating the user's brain waves to the service execution module 300-$p$.

The sensor drive module 286-13 causes the viewpoint detection sensor 186 attached to the user's head or the like to operate and detect whether or not the user is viewing any position (viewpoint) of the Web content displayed on the output device 148 (FIG. 2) and outputs information indicating the user's viewpoint to the service execution module 300-$p$.

The service execution module 300-($p$+2) is a so-called Web browser, and acquires a Web content from the Web server 8 and displays the Web content to the user of the mobile station 2 or fixed terminal 4 via the information creation module 310 and output device 148.

Furthermore, the service execution module 300-(p+1) reports the positions of elements included in the Web content to the service execution module 300-p.

When all sensors included in the combination of the first sensors 160 having high priority (pulsation sensor 162, perspiration sensor 164, brain wave sensor 168 and viewpoint detection sensor 186; FIG. 15) are available, the service execution module 300-p associates information indicating the user's viewpoint obtained by the viewpoint detection sensor 186 with the positions of the elements of the Web content inputted from the service execution module 300-(p+2) and detects the elements (advertisement/banner/photo/text or the like) of the Web content viewed by the user.

Furthermore, the service execution module 300-p processes the information obtained from the pulsation sensor 162, perspiration sensor 164 and brain wave sensor 168, and judges whether or not the user is interested in the element he/she is viewing.

When the service execution module 300 judges that the user is interested in any one element of the Web content, the service execution module 300-(p+1) processes the information obtained from the pulsation sensor 162, perspiration sensor 164 and brain wave sensor 168, and quantitatively calculates the degree of interest.

The information creation module 310 associates the element in which the user is interested with the information on the degree of interest and outputs the element to the output device 148 or the like as the result of the information service in a predetermined format.

When one or more sensors included in the combination of the first sensors 160 with high priority (pulsation sensor 162, perspiration sensor 164, brain wave sensor 168 and viewpoint detection sensor 186) are not available and the combination of the second sensors 160 with low priority (pulsation sensor 162 and perspiration sensor 164) is available, the service execution module 300-p processes the information obtained through the pulsation sensor 162 and perspiration sensor 164, associates the information with the elements of the Web content displayed on the output device 148 at each time and the display time thereof or the like and estimates whether the user is interested in any element.

When the service execution module 300 estimates that the user is interested in any one element of the Web content, the service execution module 300-(p+1) processes the information obtained from the pulsation sensor 162 and perspiration sensor 164, and quantitatively calculates the degree of interest.

The information creation module 310 associates the element in which the user is interested with the information indicating the degree of interest and outputs the element to the output device 148 or the like as a result of the information service in a predetermined format.

When the component of the Web data in which the user is interested detected as described above indicates the location of the information on a URL or the like, the service execution module 300-(p+1) acquires the information indicated by the element according to the user's predetermined operation or automatically, and outputs the information to the output device 148 or the like via the information creation module 310.

Hereinafter, the processing by the terminal program 20 when there are three or more combinations of the sensors 160 to realize a certain information service will be explained.

Figure 20:
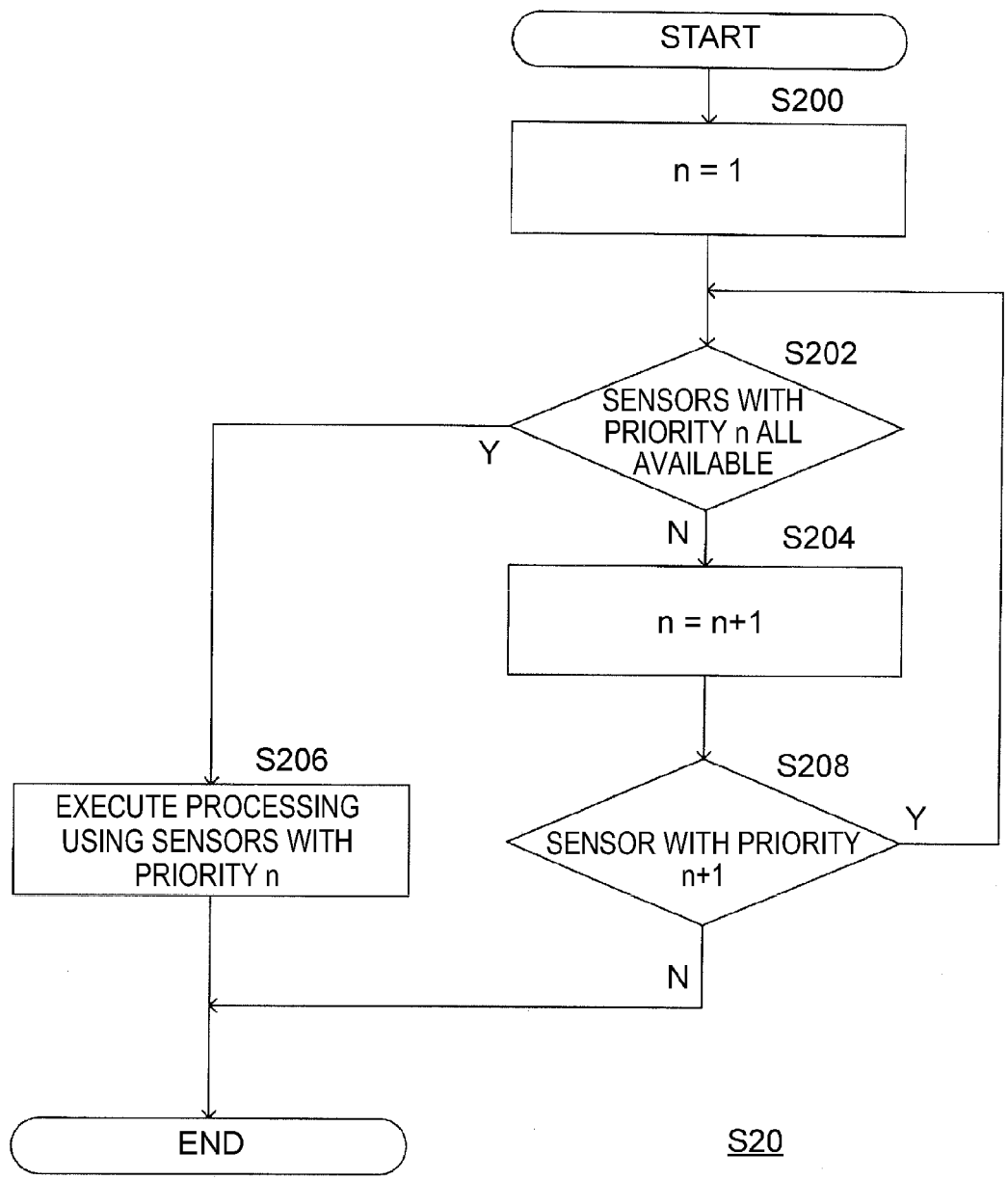
FIG. 20 is a flowchart illustrating processing (S20) of a terminal program (FIG. 4) when there are three or more sensor combinations to realize a certain information service.

FIG. 20 is a flowchart illustrating processing (S20) of the terminal program 20 (FIG. 4) when there are three or more combinations of the sensors 160 to realize a certain information service.

As shown in FIG. 20, in step 200 (S200), when the processing starts, the terminal program 20 initializes parameter n to 1.

In step 202 (S202), the terminal program 20 judges whether or not all sensors 160 included in the combination of the sensors 160 (sensor drive module 286) with the nth priority are available.

When all sensors 160 included in the combination of sensors 160 with the nth priority are available, the terminal program 20 moves to processing in S206 or moves to processing in S204 otherwise.

In step 204 (S204), the terminal program 20 increments parameter n (n=n+1).

In step 206 (S206), the terminal program 20 performs processing for delivering an information service using the combination of the sensors 160 with the nth priority.

In step 208 (S208), the terminal program 20 judges whether or not there is a combination of sensors 160 with the (n+1)th priority.

When there is a combination of sensors 160 with the (n+1)th priority, the terminal program 20 returns to the processing in S202 or ends the processing otherwise.

It is easily understandable for those skilled in the art that the processing of the terminal program 20 shown as the second embodiment is applicable to the aforementioned first to third information services in the first embodiment.

The above described embodiments have been presented for illustrations and explanations, and do not completely cover the embodiments disclosed in the present application.

Furthermore, the above described embodiments are not intended to limit the technical scope disclosed in the present application and may be altered or modified in various ways in view of the disclosed contents thereof.

Furthermore, the above described embodiments have been selected and described so as to be able to describe the principles and actual applications of the disclosed contents in the best way, and therefore those skilled in the art may use the disclosure of the present application and the embodiments thereof by adding various modifications to make the disclosure of the present application and the embodiments thereof most suitable for all possible actual applications.

Furthermore, the technical scope disclosed in the present application is intended to be defined by the descriptions and equivalents thereof.

The disclosure of the present application is applicable to a delivery of a health check service.

What is claimed is:

1. A health check system comprising:
a module and parameter delivering apparatus; and
a health check apparatus connected to the module and parameter delivering apparatus, wherein the module and parameter delivering apparatus is configured to deliver to the health check apparatus one or more module components in response to a request from the health check apparatus, the one or more module components comprising:
one or more sensor drive modules;
one or more service execution modules;
one or more output modules;
one or more sensor setting parameters set in corresponding respective sensor drive modules;
one or more processing setting parameters set in corresponding respective service execution modules; and
one or more output setting parameters set in corresponding respective output modules,
wherein the health check apparatus is configured to execute the one or more sensor drive modules, the one or more service execution modules, and the one or more output modules, and wherein the health check apparatus comprises:

an input device configured to receive an input that specifies a health check service;

a selector configured to select the module components to realize the health check service based on association information that associates the health check service with the module components to realize the health check service;

an information acquisition section configured to request, from the module and parameter delivering apparatus, module components to realize the specified health check service which do not exist in the health check apparatus;

a plurality of types of physiological sensors that match the one or more sensor drive modules and that are configured to detect physiological information from health check targets according to types thereof;

a parameter setting section configured to set a physiological sensor setting parameter, the one or more processing setting parameters, and the one or more output setting parameters in the one or more sensor drive modules the one or more service execution modules, and the one or more output modules;

an execution device that corresponds to the health check service, wherein the execution device is configured to:

execute one or more sensor drive modules, the one or more service execution modules, and the one or more output modules, and deliver information inputted or outputted to or from the one or more sensor drive modules, the one or more service execution modules, and the one or more output modules so as to match realization of the specified health check service and realize the health check service; and an output device configured to output results of the health check service, wherein the executed one or more sensor drive modules are configured to:

drive a corresponding physiological sensor, detect physiological information corresponding to the type of the corresponding physiological sensor, and output the physiological information as physiological sensor information;

wherein the one or more executed service execution modules are configured to process the physiological sensor information outputted from the corresponding physiological sensor driven by the one or more executed sensor drive modules, and output to the output module one or more of the physiological sensor information or a health condition judgment result of a health check target to which a physiological sensor is attached, wherein priority is assigned to the respective physiological sensors in the health check service, and wherein the execution device is configured to execute at least one of the selected one or more sensor drive modules to drive the respective physiological sensors in accordance with the priority assigned to respective physiological sensors, and wherein the executed one or more output modules are configured to:

create a result of the health check service from the judgment result outputted from the one or more service execution modules and the physiological sensor information, and output the created result to the output device.

2. A health check apparatus comprising:

one or more sensor drive modules;

one or more service execution modules;

an input device configured to receive an input specifying a health check service;

a selector configured to select the one or more sensor drive modules and the one or more service execution modules to realize the specified health check service based on association information that associates a plurality of health check services with the one or more sensor drive modules and the one or more service execution modules;

a plurality of types of physiological sensors corresponding to the one or more sensor drive modules, wherein the physiological sensors are configured to detect physiological information from health check targets according to the types thereof;

an execution device configured to:

execute the selected one or more sensor drive modules and the selected one or more service execution modules, and deliver information inputted or outputted between the one or more sensor drive modules and the one or more service execution modules so as to match realization of the specified health check service and realize the specified health check service; and an output device configured to output a result of the health check service, wherein the executed one or more sensor drive modules are configured to:

drive a corresponding physiological sensor, detect physiological information of the health check target corresponding to the type of the physiological sensor, and output the physiological information as physiological sensor information, wherein priority is assigned to the respective physiological sensors in the health check service, and wherein the execution device is configured to execute at least one of the selected one or more sensor drive modules to drive the respective physiological sensors in accordance with the priority assigned to respective physiological sensors, and wherein the executed one or more service execution modules are configured to:

process the physiological sensor information outputted from the executed one or more sensor drive modules, and output a processing result to the output device as a result of the health check service.

3. The health check apparatus according to claim 2, further comprising one or more output modules configured to:

process the processing result outputted from the executed one or more service execution modules, create a result of the health check service in a predetermined format, and output the created result of the health check service to the output device.

4. The health check apparatus according to claim 2, further comprising:

one or more sensor setting parameters set in corresponding respective sensor drive modules;

one or more processing setting parameters set in corresponding respective service execution modules; and a parameter setting section configured to set the one or more sensor setting parameters and the one or more processing setting parameters in the corresponding respective sensor drive modules and the corresponding respective service execution modules, wherein the selector is further configured to select one or more of the one or more sensor setting parameters and one or more of the one or more processing setting parameters necessary to realize the health check service based on the association information, wherein the association information further associates a plurality of health check services with one or more of the one or more sensor setting parameters and one or more of the one or more processing setting parameters considered necessary for realization thereof, and wherein the execution device is configured to execute the one or more sensor drive modules and the one or more service execution modules for which the settings have been made.

5. The health check apparatus according to claim 3, further comprising:
one or more sensor setting parameters set in corresponding respective sensor drive modules;
one or more processing setting parameters set in corresponding respective service execution modules; and
one or more output setting parameters set in corresponding respective output modules; and
a parameter setting section configured to set the one or more sensor setting parameters, the one or more processing setting parameters, and the one or more output setting parameters in the corresponding respective sensor drive modules, the corresponding respective service execution modules, and the corresponding respective output modules, wherein the selector is further configured to select one or more of the one or more sensor setting parameters, one or more of the one or more processing setting parameters, and one or more of the one or more output setting parameters to realize the health check service based on the association information, wherein the association information further associates a plurality of health check services, one or more of the one or more sensor setting parameters, one or more of the one or more processing setting parameters, and the one or more output modules for realization thereof, and wherein the execution device is configured to:
execute the one or more sensor drive modules, the one or more service execution modules, and the one or more output modules for which the settings have been made, deliver information inputted or outputted to or from the one or more sensor drive modules, the one or more service execution modules, and the one or more output modules so as to match the realization of the specified health check service and realize the health check service.

6. The method of claim 2, wherein the execution device is configured to deliver physiological sensor information outputted from the respective physiological sensors to one or more of the one or more service execution modules according to the priority assigned to the respective physiological sensors in the health check service.

7. The health check apparatus according to claim 2, wherein the health check service is assigned priority on realization thereof, and wherein the execution device is configured to realize the health check service according to the priority assigned to the health check service.

8. The health check apparatus according to claim 4, further comprising:
a module delivering device configured to deliver, in response to a request, one or more of:
the one or more sensor drive modules;
the one or more service execution modules;
the one or more sensor setting parameters; and
the one or more processing setting parameters; and
an information acquisition section configured to request one or more of:
the one or more sensor drive modules;
the one or more service execution modules;
the one or more sensor setting parameters; and
the one or more processing setting parameters, and wherein the selector is configured to assume one or more of:
the one or more sensor drive modules;
the one or more service execution modules;
the one or more sensor setting parameters; and
the one or more processing setting parameters.

9. The health check apparatus according to claim 5, further comprising:
a module delivering device configured to deliver, in response to a request, one or more of:
the one or more sensor drive modules;
the one or more service execution modules;
the one or more output modules;
the one or more sensor setting parameters;
the one or more processing setting parameters; and
the one or more output setting parameters, and
an information acquisition section configured to request one or more of:
the one or more sensor drive modules;
the one or more service execution modules;
the one or more output modules;
the one or more sensor setting parameters;
the one or more processing setting parameters; and
the one or more output setting parameters, and
wherein the selector is configured to assume one or more of:
the one or more sensor drive modules;
the one or more service execution modules;
the one or more output modules;
the one or more sensor setting parameters;
the one or more processing setting parameters; and
the one or more output setting parameters, delivered from a module and parameter delivering apparatus as selection targets.

10. The health check system according to claim 1, wherein the physiological sensors are configured to detect one or more of perspiration, pulsation, blood pressure, a signal generated by the heart, brain waves, or a blood component of a health check target as the physiological information.

11. An information service delivering method which is a health check method, comprising:
receiving an input specifying a health check service;
selecting one or more sensor drive modules and one or more service execution modules to realize the health check service based on association information that associates a plurality of health check services with the one or more sensor drive modules and the one or more service execution modules for realization thereof;
executing the selected one or more sensor drive modules and the selected one or more service execution modules;
delivering information inputted or outputted between the selected one or more sensor drive and the selected one or more service execution modules so as to match the realization of the health check service and thereby realize the specified health check service; and
outputting a result of the health check service,
wherein the respective executed one or more sensor drive modules are configured to:
drive a plurality of types of physiological sensors that match the respective executed one or more sensor drive modules,
detect physiological information of a health check target corresponding to the type of the respective physiological sensor, and
output the physiological information as physiological sensor information, wherein priority is assigned to the respective physiological sensors in the health check service such that the execution device is configured to execute at least one of the selected one or more sensor drive modules to drive the respective physiological sensors in accordance with the priority assigned to respective physiological sensors, and wherein the respective executed one or more service execution modules are configured to process the physiological sensor information outputted from the executed sensor drive module and output a processing result as a result of the health check service.

12. The method of claim 11, further comprising:
processing the processing result outputted from the executed one or more service execution modules;
creating a result of the health check service in a predetermined format; and
outputting, using one or more output modules, the created result of the health check service to the output device.

13. The method of claim 11, further comprising:
setting one or more sensor setting parameters in corresponding respective sensor drive modules;
setting one or more processing setting parameters in corresponding respective service execution modules; and
setting, using a parameter setting section, the one or more sensor setting parameters and the one or more processing setting parameters in the corresponding respective sensor drive modules and the corresponding respective service execution modules, wherein one or more of the one or more sensor setting parameters and one or more of the one or more processing setting parameters necessary to realize the health check service based on the association information are selected, wherein a plurality of health check services are associated with at least one of the one or more sensor setting parameters and at least one of the one or more processing setting parameters considered necessary for realization thereof, and wherein the execution device is configured to execute the one or more sensor drive modules and the one or more service execution modules for which the settings have been made.

14. The method of claim 11, wherein the execution device is configured to deliver physiological sensor information outputted from the respective physiological sensors to one or more of the one or more service execution modules according to the priority assigned to the respective physiological sensors in the health check service.

15. The method of claim 11, wherein the execution device is configured to realize the health check service according to a priority assigned to the health check service.

16. The method of claim 11, wherein the physiological sensors are configured to detect one or more of perspiration, pulsation, blood pressure, a signal generated by the heart, brain waves, or a blood component of a health check target as the physiological information.

17. The health check system of claim 1, the execution device is configured to deliver physiological sensor information outputted from the respective physiological sensors to one or more of the one or more service execution modules according to the priority assigned to the respective physiological sensors in the health check service.

18. The health check system of claim 1, wherein the execution device is configured to realize the health check service according to a priority assigned to the health check service.

19. The health check apparatus of claim 2, wherein the physiological sensors are configured to detect one or more of perspiration, pulsation, blood pressure, a signal generated by the heart, brain waves, or a blood component of a health check target as the physiological information.

* * * * *

UNITED STATES PATENT AND TRADEMARK OFFICE
CERTIFICATE OF CORRECTION

PATENT NO. : 8,583,452 B2
APPLICATION NO. : 12/640967
DATED : November 12, 2013
INVENTOR(S) : Takano et al.

It is certified that error appears in the above-identified patent and that said Letters Patent is hereby corrected as shown below:

In the Specification

In Column 1, Line 18, delete "20th TASTED" and insert -- 20th IASTED --, therefor.

In Column 12, Line 30, delete "perspiration sensor 164," and insert -- perspiration sensor 162, --, therefor.

In Column 18, Line 10, delete "pulsation sensor 162," and insert -- pulsation sensor 164, --, therefor.

In Column 18, Line 56, delete "pulsation sensor 162," and insert -- pulsation sensor 164, --, therefor.

In Column 18, Line 65, delete "pulsation sensor 162" and insert -- pulsation sensor 164 --, therefor.

In Column 19, Lines 3-4, delete "pulsation sensor 162, perspiration sensor 164," and insert -- pulsation sensor 164, perspiration sensor 162, --, therefor.

In Column 19, Lines 8-9, delete "pulsation sensor 162," and insert -- pulsation sensor 164, --, therefor.

In Column 21, Line 29, delete "pulsation sensor 162." and insert -- pulsation sensor 164. --, therefor.

In Column 22, Lines 7-8, delete "(pulsation sensor 162, perspiration sensor 164," and insert -- (pulsation sensor 164, perspiration sensor 162, --, therefor.

In Column 22, Lines 10-11, delete "(pulsation sensor 162 and perspiration sensor 164)" and insert -- (pulsation sensor 164 and perspiration sensor 162) --, therefor.

In Column 22, Lines 25-26, delete "pulsation sensor 162, perspiration sensor 164," and insert -- pulsation sensor 164, perspiration sensor 162, --, therefor.

Signed and Sealed this
Thirteenth Day of May, 2014

Michelle K. Lee
*Deputy Director of the United States Patent and Trademark Office*

In Column 23, Line 36, delete "pulsation sensor 162, perspiration sensor 164," and insert -- pulsation sensor 164, perspiration sensor 162, --, therefor.

In Column 24, Lines 41-42, delete "pulsation sensor 162" and insert -- pulsation sensor 164 --, therefor.

In Column 24, Lines 46-47, delete "perspiration sensor 164" and insert -- perspiration sensor 162 --, therefor.

In Column 25, Lines 5-6, delete "(pulsation sensor 162, perspiration sensor 164," and insert -- (pulsation sensor 164, perspiration sensor 162, --, therefor.

In Column 25, Lines 15-16, delete "pulsation sensor 162, perspiration sensor 164" and insert -- pulsation sensor 164, perspiration sensor 162 --, therefor.

In Column 25, Lines 22-23, delete "pulsation sensor 162, perspiration sensor 164" and insert -- pulsation sensor 164, perspiration sensor 162 --, therefor.

In Column 25, Lines 31-32, delete "(pulsation sensor 162, perspiration sensor 164," and insert -- (pulsation sensor 164, perspiration sensor 162, --, therefor.

In Column 25, Lines 34-35, delete "(pulsation sensor 162 and perspiration sensor 164)" and insert -- (pulsation sensor 164 and perspiration sensor 162) --, therefor.

In Column 25, Line 37, delete "pulsation sensor 162 and perspiration sensor 164," and insert -- pulsation sensor 164 and perspiration sensor 162, --, therefor.

In Column 25, Lines 45-46, delete "pulsation sensor 162 and perspiration sensor 164," and insert -- pulsation sensor 164 and perspiration sensor 162, --, therefor.

In the Claims

In Column 27, Line 13, in Claim 1, delete "the specified health" and insert -- the health --, therefor.

In Column 27, Line 33, in Claim 1, delete "the specified health" and insert -- the health --, therefor.

In Column 28, Line 27, in Claim 2, delete "the health check" and insert -- a health check --, therefor.

In Column 29, Line 45, in Claim 6, delete "The method of claim 2," and insert -- The health check apparatus according to claim 2, --, therefor.